US008420325B2

(12) United States Patent
Loeb et al.

(10) Patent No.: US 8,420,325 B2
(45) Date of Patent: *Apr. 16, 2013

(54) THERMOSTABLE POLYMERASES HAVING ALTERED FIDELITY AND METHODS OF IDENTIFYING AND USING SAME

(75) Inventors: Lawrence A. Loeb, Bellevue, WA (US); Leroy Hood, Seattle, WA (US); Motoshi Suzuki, Nogoya (JP)

(73) Assignee: University of Washington Through Its Center for Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/939,798

(22) Filed: Nov. 4, 2010

(65) Prior Publication Data

US 2011/0143356 A1    Jun. 16, 2011

Related U.S. Application Data

(63) Continuation of application No. 11/962,067, filed on Dec. 20, 2007, now abandoned, which is a continuation of application No. 11/096,645, filed on Mar. 31, 2005, now Pat. No. 7,312,059, which is a continuation of application No. 09/972,834, filed on Oct. 4, 2001, now Pat. No. 6,982,144, which is a continuation of application No. 08/978,806, filed on Nov. 26, 1997, now Pat. No. 6,395, 524.

(60) Provisional application No. 60/031,496, filed on Nov. 27, 1996.

(51) Int. Cl.
C12Q 1/68  (2006.01)
C12P 19/34  (2006.01)
C07K 1/00  (2006.01)

(52) U.S. Cl.
USPC ........... 435/6.12; 435/6.1; 435/6.11; 530/350

(58) Field of Classification Search .......................... None
See application file for complete search history.

(56) References Cited

U.S. PATENT DOCUMENTS

| | | | |
|---|---|---|---|
| 5,614,365 A | 3/1997 | Tabor et al. |
| 5,939,292 A | 8/1999 | Gelfand et al. |
| 5,945,312 A | 8/1999 | Goodman et al. |
| 5,948,614 A | 9/1999 | Chatterjee |
| 5,976,842 A | 11/1999 | Wurst |
| 6,015,668 A | 1/2000 | Hughes et al. |
| 6,395,524 B2 | 5/2002 | Loeb et al. |
| 6,982,144 B2 | 1/2006 | Loeb et al. |
| 7,312,059 B2 | 12/2007 | Loeb et al. |
| 2009/0004656 A1 | 1/2009 | Loeb et al. |

FOREIGN PATENT DOCUMENTS

| | | |
|---|---|---|
| EP | 0416801 A3 | 8/1990 |
| EP | 0655506 | 11/1994 |
| EP | 0727496 | 11/1994 |
| GB | 2302590 | 1/1997 |
| WO | 91/02090 | 2/1991 |
| WO | 95/14782 | 6/1995 |
| WO | 95/33853 | 12/1995 |
| WO | 96/10640 | 4/1996 |
| WO | 96/34980 | 11/1996 |
| WO | 96/41014 | 12/1996 |

OTHER PUBLICATIONS

Barnes, "PCR Amplification of up to 35-kb DNA with High-fidelity and High Yield From λ Bacteriophage Templates," Proc. Natl. Acad. Sci. USA 91:2216-2220 (1994).

Barnes, "The Fidelity of Taq Polymerase Catalyzing PCR is Improved by an N-terminal Deletion," Gene 112:29-35 (1992).

Bebenek et al., "The Fidelity of DNA Synthesis Catalyzed by Derivatives of *Escheria coli* DNA polymerase I," J. Biol. Chem. 265:13878-13887 (1990).

Beese et al "Structure of DNA Polymerase I Klenow Fragment Bound to Duplex DNA," Science 260:352-355 (1993).

Bell et al., "Base Miscoding and Strand Misalignment Errors by Mutator Klenow Polymerases with Amino Acid Substitutions at tTyrosine 766 in the O Helix of the Fingers Subdomain," J. Biol. Chem. 272:7345-7351 (1997).

Braithwaite & Ito, "Compilation, Alignment, and Phylogenetic Relationships of DNA Polymerases," Nucleic Acids Res. 21:787-802 (1993).

Carroll et al., "A Mutant of DNA Polymerase I (Klenow Fragment) with Reduced Fidelity," Biochem. 30:804-813 (1991).

Dong & Wang, "Mutational Studies of Human DNA Polymerase α," J. Biol. Chem. 270:121563-21570 (1995).

Drosopoulos & Prasad, "Increased Polymerase Fidelity of E89G, a Nucleoside Analog-resistant Variant of Human Immunodeficiency Virus Type 1 Reverse Transcriptase," J. Virol. 70:4834-4838 (1996).

(Continued)

*Primary Examiner* — Young J Kim
(74) *Attorney, Agent, or Firm* — Nixon Peabody LLP; Mark J. FitzGerald

(57) ABSTRACT

The present invention provides a method for identifying a thermostable polymerase having altered fidelity. The method consists of generating a random population of polymerase mutants by mutating at least one amino acid residue of a thermostable polymerase and screening the population for one or more active polymerase mutants by genetic selection. For example, the invention provides a method for identifying a thermostable polymerase having altered fidelity by mutating at least one amino acid residue in an active site O-helix of a thermostable polymerase. The invention also provides thermostable polymerases and nucleic acids encoding thermostable polymerases having altered fidelity, for example, high fidelity polymerases and low fidelity polymerases. The invention additionally provides a method for identifying one or more mutations in a gene by amplifying the gene with a high fidelity polymerase. The invention further provides a method for accurately copying repetitive nucleotide sequences using a high fidelity polymerase mutant. The invention also provides a method for diagnosing a genetic disease using a high fidelity polymerase mutant. The invention further provides a method for randomly mutagenizing a gene by amplifying the gene using a low fidelity polymerase mutant.

28 Claims, 7 Drawing Sheets

OTHER PUBLICATIONS

Dube & Loeb, "Artificial Mutants Generated by the Insertion of Random Oligonucleotides into the Putative Nucleoside Binding Site of the HSV-1 Thymidine Kinase Gene," Biochem. 30:11760-11767 (1991).

Eger et al., "Mechanism of DNA replication fidelity for three mutants of DNA polymerase I: klenow fragment (KF(exo'), KF (polA5), and KF(exo-)," Biochem. 30:1441-1448 (1 991).

Fry & Loeb, Animal Cell DNA Polymerases, 57-183 (CRC Press Boca Raton, FL 1986).

Joyce & Steitz, "Function and Structure Relationships in DNA Polymerases," Annu. Rev. Biochem. 63:777-822 (1994).

Kim & Loeb, "Human Immunodeficiency Virus Reverse Transcriptase Substitutes for DNA Polymerase I in *Escherichia coli*," Proc. Natl. Acad. Sci. USA 92:684-688 (1995).

Kim et al., "Crystal Structure of the Thermus aquaticus DNA Polymerase," Nature 376:612-616 (1995).

Kunkel, "DNA Replication Fidelity," J. Biol. Chem. 267:18251-18254 (1992).

Kunkel, "Rapid and Efficient Site-specific Mutagenesis Without Phenotypic Selection," Proc. Natl. Acad. Sci. USA 82:488-492 (1985).

Kunkel & Loeb, "On the Fidelity of DNA Replication: Effect of Divalent Metal Ion Activators and Deoxyribonucleoside Triphoshate Pools on in vitro Mutagenesis," J. Biol. Chem, 254:5718-5725 (1979).

Lawyer et al., "Isolation, Characterization, and Expression in *Escheria coli* of the DNA Polymerase Gene from *Thermus aquaticus*," J. Biol. Chem. 264:6427-6437 (1989).

Loeb, "Microsatellite Instability: Marker of a Mutator Phenotype in Cancer," Cancer Res. 54:5059-5063 (1994).

Loeb, "Unnatural Nucleotide Sequences in Biopharmaceutics," Adv. Pharmacol. 35:321-347 (1996).

Newcomb et al., "High Fidelity Taq Polymerases for Mutation Detection," FASEB J. 11:A1249, abstract 2295 (1997).

Pandey et al., "Role of Methionine 184 of Human Immunodeficiency Virus Type-1 Reverse Transcriptase in the Polymerase Function and Fidelity of DNA Synthesis," Biochem. 35:2168-2179 (1996).

Reha-Krantz & Nonay, "Motif A of Bacteriophage T4 DNA Polymerase: Role in Primer Extension and DNA Replication Fidelity," J. Biol. Chem. 269:5635-5643 (1994).

Suzuki et al., "Low Fidelity Mutants in the O-helix of *Thermus aquaticus* DNA Polymerase I," J. Biol. Chem. 272:11228-11235 (1997).

Suzuki et al., "Random Mutagenesis of Thermus aquaticus DNA Polymerase I: Concordance of Immutable Sites in vivo with the Crystal Structure," Proc. Natl. Acad. Sci. USA 93:9670-9675 (1996).

Sweasy & Loeb, "Mammalian DNA Polymerase β can Substitute for DNA Polymerase I During DNA Replication in *Escherichia coli*," J. Biol. Chem. 267:1407-1410 (1992).

Tabor & Richardson, "A Single Residue in DNA Polymerases of the *Escherichia coli* DNA Polymerase I Family is Critical for Distinguishing Between Deoxy- and Dideoxyribonucleotides," Proc. Natl. Acad. Sci. USA 92:6339-6343 (1995).

Tindall & Kunkel, "Fidelity of DNA Synthesis by the *Themius aquaticus* DNA Polymerase," Biochem. 27:6008-6013 (1988).

Wainberg er al., "Enhanced Fidelity of 3TC-selected Mutant HIV-1 Reverse Transcriptase," Science 271:1282-1285 (1996).

Washington et al., "A Genetic System to Identify DNA Polymerase β Mutator Mutants," Proc. Natl. Acad. Sci. USA 94:1321-1326 (1997).

Mao et al., "Microsatellite Alterations as Clonal Markers for the Detection of Human Cancer," Proc. Natl. Acad. Sci. USA 91:9871-9875 (1994).

International Preliminary Examination Report for PCT/US97/21940 (Feb. 26, 1999).

Written Opinion for PCT/US97/21940 (Sep. 9, 1998).

International Search Report for PCT/US97/21940 (May 7, 1998).

```
AAGCTCAGAT CTACCTGCCT GAGGGCGTCC GGTTCCAGCT GGCCCTTCCC GAGGGGGAGA    60
GGGAGGCGTT TCTAAAAGCC CTTCAGGACG CTACCCGGGG GCGGGTGGTG GAAGGGTAAC   120

ATG AGG GGG ATG CTG CCC CTC TTT GAG CCC AAG GGC CGG GTC CTC CTG    168
Met Arg Gly Met Leu Pro Leu Phe Glu Pro Lys Gly Arg Val Leu Leu
 1           5                  10                 15

GTG GAC GGC CAC CAC CTG GCC TAC CGC ACC TTC CAC GCC CTG AAG GGC    216
Val Asp Gly His His Leu Ala Tyr Arg Thr Phe His Ala Leu Lys Gly
              20                  25                  30

CTC ACC ACC AGC CGG GGG GAG CCG GTG CAG GCG GTC TAC GGC TTC GCC    264
Leu Thr Thr Ser Arg Gly Glu Pro Val Gln Ala Val Tyr Gly Phe Ala
         35                  40                  45

AAG AGC CTC CTC AAG GCC CTC AAG GAG GAC GGG GAC GCG GTG ATC GTG    312
Lys Ser Leu Leu Lys Ala Leu Lys Glu Asp Gly Asp Ala Val Ile Val
     50                  55                  60

GTC TTT GAC GCC AAG GCC CCC TCC TTC CGC CAC GAG GCC TAC GGG GGG    360
Val Phe Asp Ala Lys Ala Pro Ser Phe Arg His Glu Ala Tyr Gly Gly
 65                  70                  75                  80

TAC AAG GCG GGC CGG GCC CCC ACG CCG GAG GAC TTT CCC CGG CAA CTC    408
Tyr Lys Ala Gly Arg Ala Pro Thr Pro Glu Asp Phe Pro Arg Gln Leu
             85                  90                  95

GCC CTC ATC AAG GAG CTG GTG GAC CTC CTG GGG CTG GCG CGC CTC GAG    456
Ala Leu Ile Lys Glu Leu Val Asp Leu Leu Gly Leu Ala Arg Leu Glu
             100                 105                 110

GTC CCG GGC TAC GAG GCG GAC GAC GTC CTG GCC AGC CTG GCC AAG AAG    504
Val Pro Gly Tyr Glu Ala Asp Asp Val Leu Ala Ser Leu Ala Lys Lys
         115                 120                 125

GCG GAA AAG GAG GGC TAC GAG GTC CGC ATC CTC ACC GCC GAC AAA GAC    552
Ala Glu Lys Glu Gly Tyr Glu Val Arg Ile Leu Thr Ala Asp Lys Asp
 130                 135                 140

CTT TAC CAG CTC CTT TCC GAC CGC ATC CAC GTC CTC CAC CCC GAG GGG    600
Leu Tyr Gln Leu Leu Ser Asp Arg Ile His Val Leu His Pro Glu Gly
145                 150                 155                 160

TAC CTC ATC ACC CCG GCC TGG CTT TGG GAA AAG TAC GGC CTG AGG CCC    648
Tyr Leu Ile Thr Pro Ala Trp Leu Trp Glu Lys Tyr Gly Leu Arg Pro
             165                 170                 175

GAC CAG TGG GCC GAC TAC CGG GCC CTG ACC GGG GAC GAG TCC GAC AAC    696
Asp Gln Trp Ala Asp Tyr Arg Ala Leu Thr Gly Asp Glu Ser Asp Asn
         180                 185                 190

CTT CCC GGG GTC AAG GGC ATC GGG GAG AAG ACG GCG AGG AAG CTT CTG    744
Leu Pro Gly Val Lys Gly Ile Gly Glu Lys Thr Ala Arg Lys Leu Leu
    195                 200                 205
```

FIG. 1A

```
GAG GAG TGG GGG AGC CTG GAA GCC CTC CTC AAG AAC CTG GAC CGG CTG          792
Glu Glu Trp Gly Ser Leu Glu Ala Leu Leu Lys Asn Leu Asp Arg Leu
    210             215                 220
AAG CCC GCC ATC CGG GAG AAG ATC CTG GCC CAC ATG GAC GAT CTG AAG          840
Lys Pro Ala Ile Arg Glu Lys Ile Leu Ala His Met Asp Asp Leu Lys
225             230                 235                 240
CTC TCC TGG GAC CTG GCC AAG GTG CGC ACC GAC CTG CCC CTG GAG GTG          888
Leu Ser Trp Asp Leu Ala Lys Val Arg Thr Asp Leu Pro Leu Glu Val
                245                 250                 255
GAC TTC GCC AAA AGG CGG GAG CCC GAC CGG GAG AGG CTT AGG GCC TTT          936
Asp Phe Ala Lys Arg Arg Glu Pro Asp Arg Glu Arg Leu Arg Ala Phe
                260                 265                 270
CTG GAG AGG CTT GAG TTT GGC AGC CTC CTC CAC GAG TTC GGC CTT CTG          984
Leu Glu Arg Leu Glu Phe Gly Ser Leu Leu His Glu Phe Gly Leu Leu
        275                 280                 285
GAA AGC CCC AAG GCC CTG GAG GAG GCC CCC TGG CCC CCG CCG GAA GGG         1032
Glu Ser Pro Lys Ala Leu Glu Glu Ala Pro Trp Pro Pro Pro Glu Gly
        290                 295                 300
GCC TTC GTG GGC TTT GTG CTT TCC CGC AAG GAG CCC ATG TGG GCC GAT         1080
Ala Phe Val Gly Phe Val Leu Ser Arg Lys Glu Pro Met Trp Ala Asp
305             310                 315                 320
CTT CTG GCC CTG GCC GCC GCC AGG GGG GGC CGG GTC CAC CGG GCC CCC         1128
Leu Leu Ala Leu Ala Ala Ala Arg Gly Gly Arg Val His Arg Ala Pro
                325                 330                 335
GAG CCT TAT AAA GCC CTC AGG GAC CTG AAG GAG GCG CGG GGG CTT CTC         1176
Glu Pro Tyr Lys Ala Leu Arg Asp Leu Lys Glu Ala Arg Gly Leu Leu
                340                 345                 350
GCC AAA GAC CTG AGC GTT CTG GCC CTG AGG GAA GGC CTT GGC CTC CCG         1224
Ala Lys Asp Leu Ser Val Leu Ala Leu Arg Glu Gly Leu Gly Leu Pro
        355                 360                 365
CCC GGC GAC GAC CCC ATG CTC CTC GCC TAC CTC CTG GAC CCT TCC AAC         1272
Pro Gly Asp Asp Pro Met Leu Leu Ala Tyr Leu Leu Asp Pro Ser Asn
        370                 375                 380
ACC ACC CCC GAG GGG GTG GCC CGG CGC TAC GGC GGG GAG TGG ACG GAG         1320
Thr Thr Pro Glu Gly Val Ala Arg Arg Tyr Gly Gly Glu Trp Thr Glu
385             390                 395                 400
GAG GCG GGG GAG CGG GCC GCC CTT TCC GAG AGG CTC TTC GCC AAC CTG         1368
Glu Ala Gly Glu Arg Ala Ala Leu Ser Glu Arg Leu Phe Ala Asn Leu
                405                 410                 415
TGG GGG AGG CTT GAG GGG GAG GAG AGG CTC CTT TGG CTT TAC CGG GAG         1416
Trp Gly Arg Leu Glu Gly Glu Glu Arg Leu Leu Trp Leu Tyr Arg Glu
            420                 425                 430
```

FIG. 1B

```
GTG GAG AGG CCC CTT TCC GCT GTC CTG GCC CAC ATG GAG GCC ACG GGG    1464
Val Glu Arg Pro Leu Ser Ala Val Leu Ala His Met Glu Ala Thr Gly
        435             440                 445

GTG CGC CTG GAC GTG GCC TAT CTC AGG GCC TTG TCC CTG GAG GTG GCC    1512
Val Arg Leu Asp Val Ala Tyr Leu Arg Ala Leu Ser Leu Glu Val Ala
        450             455                 460

GAG GAG ATC GCC CGC CTC GAG GCC GAG GTC TTC CGC CTG GCC GGC CAC    1560
Glu Glu Ile Ala Arg Leu Glu Ala Glu Val Phe Arg Leu Ala Gly His
465             470                 475                 480

CCC TTC AAC CTC AAC TCC CGG GAC CAG CTG GAA AGG GTC CTC TTT GAC    1608
Pro Phe Asn Leu Asn Ser Arg Asp Gln Leu Glu Arg Val Leu Phe Asp
                485                 490                 495

GAG CTA GGG CTT CCC GCC ATC GGC AAG ACG GAG AAG ACC GGC AAG CGC    1656
Glu Leu Gly Leu Pro Ala Ile Gly Lys Thr Glu Lys Thr Gly Lys Arg
                500                 505                 510

TCC ACC AGC GCC GCC GTC CTG GAG GCC CTC CGC GAG GCC CAC CCC ATC    1704
Ser Thr Ser Ala Ala Val Leu Glu Ala Leu Arg Glu Ala His Pro Ile
            515                 520                 525

GTG GAG AAG ATC CTG CAG TAC CGG GAG CTC ACC AAG CTG AAG AGC ACC    1752
Val Glu Lys Ile Leu Gln Tyr Arg Glu Leu Thr Lys Leu Lys Ser Thr
    530                 535                 540

TAC ATT GAC CCC TTG CCG GAC CTC ATC CAC CCC AGG ACG GGC CGC CTC    1800
Tyr Ile Asp Pro Leu Pro Asp Leu Ile His Pro Arg Thr Gly Arg Leu
545                 550                 555                 560

CAC ACC CGC TTC AAC CAG ACG GCC ACG GCC ACG GGC AGG CTA AGT AGC    1848
His Thr Arg Phe Asn Gln Thr Ala Thr Ala Thr Gly Arg Leu Ser Ser
                565                 570                 575

TCC GAT CCC AAC CTC CAG AAC ATC CCC GTC CGC ACC CCG CTT GGG CAG    1896
Ser Asp Pro Asn Leu Gln Asn Ile Pro Val Arg Thr Pro Leu Gly Gln
                580                 585                 590

AGG ATC CGC CGG GCC TTC ATC GCC GAG GAG GGG TGG CTA TTG GTG GCC    1944
Arg Ile Arg Arg Ala Phe Ile Ala Glu Glu Gly Trp Leu Leu Val Ala
            595                 600                 605

CTG GAC TAT AGC CAG ATA GAG CTC AGG GTG CTG GCC CAC CTC TCC GGC    1992
Leu Asp Tyr Ser Gln Ile Glu Leu Arg Val Leu Ala His Leu Ser Gly
610                 615                 620

GAC GAG AAC CTG ATC CGG GTC TTC CAG GAG GGG CGG GAC ATC CAC ACG    2040
Asp Glu Asn Leu Ile Arg Val Phe Gln Glu Gly Arg Asp Ile His Thr
625                 630                 635                 640

GAG ACC GCC AGC TGG ATG TTC GGC GTC CCC CGG GAG GCC GTG GAC CCC    2088
Glu Thr Ala Ser Trp Met Phe Gly Val Pro Arg Glu Ala Val Asp Pro
                645                 650                 655
```

FIG. 1C

```
CTG ATG CGC CGG GCG GCC AAG ACC ATC AAC TTC GGG GTC CTC TAC GGC    2136
Leu Met Arg Arg Ala Ala Lys Thr Ile Asn Phe Gly Val Leu Tyr Gly
            660                 665                 670

ATG TCG GCC CAC CGC CTC TCC CAG GAG CTA GCC ATC CCT TAC GAG GAG    2184
Met Ser Ala His Arg Leu Ser Gln Glu Leu Ala Ile Pro Tyr Glu Glu
            675                 680                 685

GCC CAG GCC TTC ATT GAG CGC TAC TTT CAG AGC TTC CCC AAG GTG CGG    2232
Ala Gln Ala Phe Ile Glu Arg Tyr Phe Gln Ser Phe Pro Lys Val Arg
            690                 695                 700

GCC TGG ATT GAG AAG ACC CTG GAG GAG GGC AGG AGG CGG GGG TAC GTG    2280
Ala Trp Ile Glu Lys Thr Leu Glu Glu Gly Arg Arg Arg Gly Tyr Val
705                 710                 715                 720

GAG ACC CTC TTC GGC CGC CGC CGC TAC GTG CCA GAC CTA GAG GCC CGG    2328
Glu Thr Leu Phe Gly Arg Arg Arg Tyr Val Pro Asp Leu Glu Ala Arg
                725                 730                 735

GTG AAG AGC GTG CGG GAG GCG GCC GAG CGC ATG GCC TTC AAC ATG CCC    2376
Val Lys Ser Val Arg Glu Ala Ala Glu Arg Met Ala Phe Asn Met Pro
            740                 745                 750

GTC CAG GGC ACC GCC GCC GAC CTC ATG AAG CTG GCT ATG GTG AAG CTC    2424
Val Gln Gly Thr Ala Ala Asp Leu Met Lys Leu Ala Met Val Lys Leu
            755                 760                 765

TTC CCC AGG CTG GAG GAA ATG GGG GCC AGG ATG CTC CTT CAG GTC CAC    2472
Phe Pro Arg Leu Glu Glu Met Gly Ala Arg Met Leu Leu Gln Val His
        770                 775                 780

GAC GAG CTG GTC CTC GAG GCC CCA AAA GAG AGG GCG GAG GCC GTG GCC    2520
Asp Glu Leu Val Leu Glu Ala Pro Lys Glu Arg Ala Glu Ala Val Ala
785                 790                 795                 800

CGG CTG GCC AAG GAG GTC ATG GAG GGG GTG TAT CCC CTG GCC GTG CCC    2568
Arg Leu Ala Lys Glu Val Met Glu Gly Val Tyr Pro Leu Ala Val Pro
                805                 810                 815

CTG GAG GTG GAG GTG GGG ATA GGG GAG GAC TGG CTC TCC GCC AAG GAG    2616
Leu Glu Val Glu Val Gly Ile Gly Glu Asp Trp Leu Ser Ala Lys Glu
            820                 825                 830

TGATACCACC                                                         2626
```

FIG. 1D

| Taq | 659 | | | 663 | | | | | 667 | | | | 671 |
|---|---|---|---|---|---|---|---|---|---|---|---|---|---|
| E.coli | 754 | | | 758 | | | | | 762 | | | | 766 |
| WT : | R | R | A | A | S | K | T | I | N | F | G | V | L | Y |
| | | S | | | S | | S | V | I | | | I | I | F |
| | | E | | | | | N | T | D | | | | T | |
| | | P | | | | | I | L | L | | | | V | |
| | | G | | | | | P | | V | | | | | |
| | | K | | | | | R | | | | | | | |
| | | R | | | | | H | | | | | | | |

FIG. 2A

| Taq | 659 | 660 | | 663 | | | | 667 | 668 | | | |
|---|---|---|---|---|---|---|---|---|---|---|---|---|
| E.coli | 754 | 755 | | 758 | | | | 762 | 763 | | | |
| WT : | R | R | A | A | K | T | I | N | F | G | V | L | Y |
| | | Y | | | | | | | Y | S | | | |
| | | P | | | | | | | | Q | | | |
| | | G | | | | | | | | R | | | |
| | | S | | | | | | | | K | | | |
| | | I | | | | | | | | | | | |
| | | K | | | | | | | | | | | |
| | | W | | | | | | | | | | | |
| | | C | | | | | | | | | | | |
| | | A | | | | | | | | | | | |

THERMOSTABLE POLYMERASES HAVING ALTERED FIDELITY AND METHODS OF IDENTIFYING AND USING SAME

CROSS-REFERENCE TO RELATED APPLICATIONS

This application is a continuation of U.S. patent application Ser. No. 11/962,067, filed Dec. 20, 2007 now abandoned, which is a continuation of U.S. patent application Ser. No. 11/096,645, filed Mar. 31, 2005, now U.S. Pat. No. 7,312,059, issued Dec. 25, 2007, which is a continuation of U.S. patent application Ser. No. 09/972,834, filed Oct. 4, 2001, now U.S. Pat. No. 6,982,144, issued Jan. 3, 2006, which is a continuation of U.S. patent application Ser. No. 08/978,806, filed Nov. 26, 1997, now U.S. Pat. No. 6,395,524, issued May 28, 2002, which claims the benefit of U.S. Provisional Patent Application Ser. No. 60/031,496, filed Nov. 27, 1996, each of which is hereby incorporated by reference in its entirety.

GOVERNMENT SUPPORT

This invention was made with government support under grant number OIG-R35-CA-39903 awarded by the National Institutes of Health and grant number B1R9214821 10 awarded by the National Science Foundation. The government has certain rights in the invention.

BACKGROUND OF THE INVENTION

The present invention relates generally to thermostable polymerases and more specifically to methods for identifying polymerase mutants having desired fidelity.

Every living organism requires genetic material, deoxyribonucleic acid (DNA), to pass a unique collection of characteristics to its offspring. Genes are discreet segments of the DNA and provide the information required to generate a new organism. Even simple organisms, such as bacteria, contain thousands of genes, and the number is many fold greater in complex organisms such as humans. Understanding the complexities of the development and functioning of living organisms requires knowledge of these genes. However, the amount of DNA that can be isolated for study has often been limiting.

A major breakthrough in the study of genes was the development of the polymerase chain reaction (PCR).

PCR amplifies genes or portions of genes by making many identical copies, allowing isolation of genes from very tiny amounts of DNA. The motors for PCR are DNA polymerases that copy the DNA of each gene during each round of DNA synthesis. Using oligonucleotides that determine the start and termination of DNA synthesis, a single gene can be replicated into millions of copies. This process has created a revolution in biotechnology and has been used extensively for the identification of mutant genes that are responsible for or associated with inherited human diseases. It is now possible to identify a mutant gene in a single cell, amplify the gene a million times, and establish the nature of the mutation. One application of identifying a mutant gene is the determination of genetic susceptibility to disease, which can be mapped by gene amplification and DNA sequencing.

DNA polymerases function in cells as the enzymes responsible for the synthesis of DNA. They polymerize deoxyribonucleoside triphosphates in the presence of a metal activator, such as $Mg^{2+}$, in an order dictated by the DNA template or polynucleotide template that is copied. Even though the template dictates the order of nucleotide subunits that are linked together in the newly synthesized DNA, these enzymes also function to maintain the accuracy of this process. The contribution of DNA polymerases to the fidelity of DNA synthesis is mediated by two mechanisms. First, the geometry of the substrate binding site in DNA polymerases contributes to the selection of the complementary deoxynucleoside triphosphates. Mutations within the substrate binding site on the polymerase can alter the fidelity of DNA synthesis. Second, many DNA polymerases contain a proof-reading 3'-5' exonuclease that preferentially and immediately excises non-complementary deoxynucleoside triphosphates if they are added during the course of synthesis. As a result, these enzymes copy DNA in vitro with a fidelity varying from $5 \times 10^{-4}$ (1 error per 2000 bases) to $10^{-7}$ (1 error per $10^7$ bases) (Fry and Loeb, *Animal Cell DNA Polymerases*, pp. 221, CRC Press, Inc., Boca Raton, Fla. (1986); Kunkel, T. A., *J. Biol. Chem.* 267 :18251-18254 (1992)).

In vivo, DNA polymerases participate in a spectrum of DNA synthetic processes including DNA replication, DNA repair, recombination, and gene amplification (Kornberg and Baker, *DNA Replication, pp.* 929, W.H. Freeman and Co., New York (1992)). During each DNA synthetic process, the DNA template is copied once or at most a few times to produce identical replicas. In vitro DNA replication, in contrast, can be repeated many times, for example, during PCR.

In the initial studies with PCR, the DNA polymerase was added at the start of each round of DNA replication. Subsequently, it was determined that thermostable DNA polymerases could be obtained from bacteria that grow at elevated temperatures, and these enzymes need to be added only once. At the elevated temperatures used during PCR, these enzymes would not denature. As a result, one can carry out repetitive cycles of polymerase chain reactions without adding fresh enzymes at the start of each synthetic addition process. The commercial market for the sale of DNA polymerases from thermostable organisms can be conservatively estimated at 200 million dollars per year. DNA polymerases, particularly thermostable polymerases, are the key to a large number of techniques in recombinant DNA studies and in medical diagnosis of disease.

Due to the importance of DNA polymerases in biotechnology and medicine, it would be highly advantageous to generate DNA polymerases having desired enzymatic properties such as altered fidelity. However, the ability to predict the effect of introducing an amino acid mutation into the sequence of a protein remains very limited. Even when structural information is available for the protein of interest, it is often very difficult to predict the effect of mutations of specific amino acid residues on the function of that protein. In particular, it is extremely difficult to predict amino acid substitutions that will alter the activity of an enzyme to achieve a desirable change.

Despite the limitations in predicting the effect of introducing amino acid substitutions into proteins, a number of mutant DNA polymerases have been discovered, or have been created by site-specific mutagenesis, and have been used in PCR amplification (Tabor and Richardson, *Proc. Natl. Acad. Sci. USA* 92:6339-6343 (1995)). Some of these mutant polymerases offer particular advantages with respect to thermostability, processivity, length of the newly synthesized DNA product, or fidelity of DNA synthesis. Those that are more accurate for the most part contain a 3'-5' exonuclease activity that removes misincorporated bases prior to adding the next nucleotide during DNA synthesis. However, the current spectrum of mutant DNA polymerases is quite limited. For the most part, these mutants have been obtained by introducing a single base substitution at a specified site, purifying the enzyme and studying the changes in catalytic activity (Joyce and Steitz, *Annu. Rev. Biochem.* 63:777-822 (1994)). These laborious and step-wise procedures have been necessary due to the lack of adequate knowledge to predict the effects of most single amino acid substitutions and due to the lack of rules for predicting the effects of multiple simultaneous substitutions.

Thus, there exists a need for rapid and efficient methods to produce and screen for modified polymerases having desired fidelity in polynucleotide synthesis. The present invention satisfies this need and provides related advantages as well.

SUMMARY OF THE INVENTION

The present invention provides a method for identifying a thermostable polymerase having altered fidelity. The method consists of generating a random population of polymerase mutants by mutating at least one amino acid residue of a thermostable polymerase and screening the population for one or more active polymerase mutants by genetic selection. For example, the invention provides a method for identifying a thermostable polymerase having altered fidelity by mutating at least one amino acid residue in an active site O-helix of a thermostable polymerase. The invention also provides thermostable polymerases and nucleic acids encoding thermostable polymerases having altered fidelity, for example, high fidelity polymerases and low fidelity polymerases. The invention additionally provides a method for identifying one or more mutations in a gene by amplifying the gene with a high fidelity polymerase. The invention further provides a method for accurately copying repetitive nucleotide sequences using a high fidelity polymerase mutant. The invention also provides a method for diagnosing a genetic disease using a high fidelity polymerase mutant. The invention further provides a method for randomly mutagenizing a gene by amplifying the gene using a low fidelity polymerase mutant.

BRIEF DESCRIPTION OF THE DRAWINGS

FIG. 1 shows the nucleotide and amino acid sequence of Taq DNA polymerase I (SEQ ID NOS:1 and 2, respectively).

FIG. 2 shows a compilation of amino acid substitutions identified in a screen of Taq DNA polymerase I mutants. Panel A shows single mutations (SEQ ID NO: 13 to SEQ ID NO: 20), which were identified in the screen of a 9% library, listed under the wild type amino acids SEQ ID NO: 12). Panel B shows the sequence of multiply substituted mutants identified in the screen of a 9% library (SEQ ID NO: 21 to SEQ ID NO: 57). Panel C shows mutations selected from a totally random library of selected amino acids (SEQ ID NO: 58 to SEQ ID NO: 60).

DETAILED DESCRIPTION OF THE INVENTION

Figure 3:
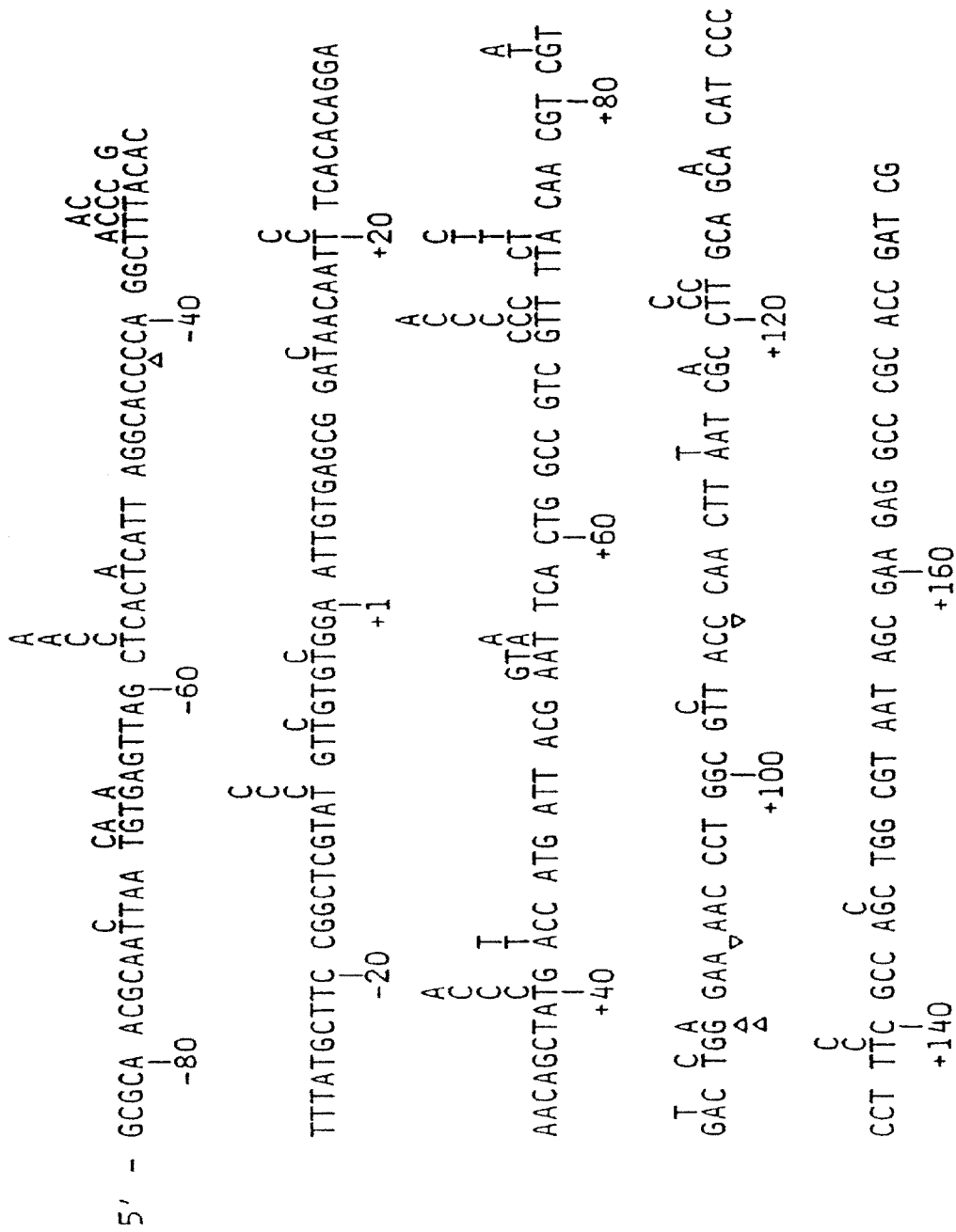
FIG. 3 shows the spectrum of single base changes generated in a forward mutation assay by Taq DNA polymerase I mutant Thr664Arg (SEQ ID NO: 61).

The invention is directed to methods for screening and identifying thermostable polymerases that have altered fidelity of DNA synthesis as well as to the resultant polymerase compositions. As disclosed herein, the invention provides rapid and efficient methods to identify polymerase mutants having altered fidelity. These methods are applicable to the identification of polymerase mutants having a desired activity such as high fidelity or low fidelity. An advantage of the methods is that they use a population of polymerase mutants to rapidly identify active polymerase mutants having altered fidelity. The identification of low fidelity mutants is useful for introducing mutations into specific genes due to the increased frequency of misincorporation of nucleotides during error-prone PCR amplification. The identification of high fidelity mutants is useful for PCR amplification of genes and for mapping of genetic mutations. The methods of the invention can therefore be advantageously applied to the identification of polymerase mutants useful for the characterization of specific genes and for the identification and diagnosis of human genetic diseases.

As used herein, the term "polymerase" is intended to refer to an enzyme that polymerizes nucleoside triphosphates. Polymerases use a template nucleic acid strand to synthesize a complementary nucleic acid strand. The template strand and synthesized nucleic acid strand can independently be either DNA or RNA. Polymerases can include, for example, DNA polymerases such as *Escherichia coli* DNA polymerase I and *Thermus aquaticus* (Taq) DNA polymerase I, DNA-dependent RNA polymerases and reverse transcriptases. The polymerase is a polypeptide or protein containing sufficient amino acids to carry out a desired enzymatic function of the polymerase. The polymerase need not contain all of the amino acids found in the native enzyme but only those which are sufficient to allow the polymerase to carry out a desired catalytic activity. Catalytic activities include, for example, 5'-3' polymerization, 5'-3' exonuclease and 3'-5' exonuclease activities.

As used herein, the term "polymerase mutant" is intended to refer to a polymerase that contains one or more amino acids that differ from a selected polymerase. The selected polymerase is determined based on desired enzymatic properties and is used as a parent polymerase to generate a population of polymerase mutants. A selected polymerase can be, for example, a wild type polymerase as isolated from an organism or can be a mutant polymerase that differs from a wild type polymerase by one or more amino acids and has desirable enzymatic properties. As disclosed herein, a thermostable polymerase such as Taq DNA polymerase I can be selected, for example, as a polymerase to generate a population of polymerase mutants.

As used herein, the term "population" is intended to refer to a group of two or more different molecular species. Molecular species differ by some detectable property such as a difference in at least one amino acid residue or at least one nucleotide residue or a difference introduced by the modification of an amino acid such as the addition of a chemical functional group. For example, a population of polymerase mutants would contain two or more different polymerase mutants. Typically, populations can be as small as two species and as large as $10^{12}$ species. In some embodiments, populations are between about five and 20 different species as well as up to-hundreds or thousands of different species. In other embodiments, populations can be, for example, greater than $10^4$, $10^5$ and $10^6$ different species. In the specific example presented in Example I, the population described therein is 50,000 different species. In yet other embodiments, populations are between about $10^6$-$10^8$ or more different species. Those skilled in the art will know a suitable size and diversity of a population sufficient for a particular application.

A population of polymerase mutants consists of two or more mutant polymerases which differ by at least one amino acid from the parent polymerase. A population of polymerase mutants can consist, for example, of multiple substitutions of a single amino acid residue where the substitutions are changes to any or all of the non-parental, naturally occurring amino acids at that amino acid position. In this example, the population would comprise nineteen members, and all members of the polymerase mutant population would consist of nineteen different amino acid substitutions at a single amino acid position. A population of polymerase mutants can also consist, for example, of at least one substitution at two or more different amino acid positions. In this example, a minimal population containing two polymerase mutants would consist of a single amino acid substitution at two different positions. Such a population can be expanded with the addition of substitutions to any or all of the 19 non-parental amino acids at these two amino acid positions or additional amino acid positions.

As used herein, the term "random" when used in reference to a population is intended to refer to a population of molecules generated without limiting the molecules to contain predetermined specific residues. Such a population excludes molecules in which a specific residue is substituted with a specific predetermined residue and individually assayed to determine its activity. The residues can be amino acid residues or nucleotide residues encoding a codon. The random molecules can be generated, for example, by introducing random nucleotides into an oligonucleotide sequence that encodes an amino acid sequence of a protein region of interest (see Example I). Thus, a random population is generated to contain random oligonucleotide sequences which can be expressed in appropriate cells to generate a random population of expressed proteins. A specific example of such a random population is the population of polymerase mutants described in Example I that were generated to screen for active polymerase mutants having altered fidelity.

As used herein, the term "catalytic activity" or "activity" when used in reference to a polymerase is intended to refer to the enzymatic properties of the polymerase. The catalytic activity includes, for example: enzymatic properties such as the rate of synthesis of nucleic acid polymers; the $K_m$ for substrates such as nucleoside triphosphates and template strand; the fidelity of template-directed incorporation of nucleotides, where the frequency of incorporation of non-complementary nucleotides is compared to that of complementary nucleotides; processivity, the number of nucleotides synthesized by a polymerase prior to dissociation from the DNA template; discrimination of the ribose sugar; and stability, for example, at elevated temperatures. Polymerases can discriminate between templates, for example, DNA polymerases generally use DNA templates and RNA polymerases generally use RNA templates, whereas reverse transcriptases use both RNA and DNA templates. DNA polymerases also discriminate between deoxyribonucleoside triphosphates and dideoxyribonucleoside triphosphates. Any of these distinct enzymatic properties can be included in the meaning of the term catalytic activity, including any single property, any combination of properties or all of the properties. Although specific embodiments identifying polymerase mutants having altered fidelity are exemplified herein, the methods of the invention can similarly be applied to identify polymerases having altered catalytic activity distinct from altered fidelity.

As used herein, the term "fidelity" when used in reference to a polymerase is intended to refer to the accuracy of template-directed incorporation of complementary bases in a synthesized DNA strand relative to the template strand. Fidelity is measured based on the frequency of incorporation of incorrect bases in the newly synthesized nucleic acid strand. The incorporation of incorrect bases can result in point mutations, insertions or deletions. Fidelity can be calculated according to the procedures described in Tindall and Kunkel (*Biochemistry* 27:6008-6013 (1988)). Methods for determining fidelity are well known in the art and include, for example, those described in Example III. A polymerase or polymerase mutant can exhibit either high fidelity or low fidelity. As used herein, the term "high fidelity" is intended to mean a frequency of accurate base incorporation that exceeds a predetermined value. Similarly, the term "low fidelity" is intended to mean a frequency of accurate base incorporation that is lower than a predetermined value. The predetermined value can be, for example, a desired frequency of accurate base incorporation or the fidelity of a known polymerase.

As used herein, the term "altered fidelity" refers to the fidelity of a polymerase mutant that differs from the fidelity of the selected parent polymerase from which the polymerase mutant is derived. The altered fidelity can either be higher or lower than the fidelity of the selected parent polymerase. Thus, polymerase mutants with altered fidelity can be classified as high fidelity polymerases or low fidelity polymerases. Altered fidelity can be determined by assaying the parent and mutant polymerase and comparing their activities using any assay that measures the accuracy of template directed incorporation of complementary bases. Such methods for measuring fidelity include, for example, those described in Example III as well as other methods known to those skilled in the art.

As used herein, the term "immutable" when used in reference to an amino acid residue is intended to refer to an amino acid residue which cannot be substituted with another amino acid residue and still retain measurable function of the polypeptide. An immutable amino acid residue can be determined by introducing one or more substitutions of an amino acid residue and assaying the resulting mutant polypeptides for polypeptide function. An immutable residue can be identified, for example, using site-directed mutagenesis to substitute each of the 19 non-parental amino acids at a given position and determining if any of these mutants are active. Random mutagenesis can also be employed to introduce substitutions of each of the nineteen, naturally occurring non-parental amino acids at a given position. Random mutagenesis can provide a statistical representation of all 20 amino acids at a given position. Sequencing of polymerase-mutants allows determination of whether a given amino acid residue can tolerate any mutations. Assays for determining the function of mutant polypeptides include in vitro enzymatic assays as well as genetic complementation assays such as those described in Example I. If substitution of an amino acid residue with any other amino acid results in loss of polypeptide function, then that amino acid residue is considered to be immutable.

As used herein, the term "nearly immutable" when used in reference to an amino acid residue is intended to refer to an amino acid residue which can only tolerate conservative substitutions and still retain polypeptide function. Conservative amino acids are known to those skilled in the art and include those amino acids which have similar structure and chemical properties. Conservative substitutions of amino acids include, for example, the identification of amino acid substitutions based on the frequencies of amino acid changes between corresponding proteins of homologous organisms (Schulz and Schirmer, *Principles of Protein Structure,* Springer Verlag, N.Y. (1979)).

As used herein, the term "substantially" or "substantially the same" when used in reference to a nucleotide or amino acid sequence is intended to mean that the function of the polypeptide encoded by the nucleotide or amino acid sequence is essentially the same as the referenced parental nucleotide or amino acid sequence. For example, changes in a nucleotide or amino acid sequence that results in substitution of amino acids that differ from the parent molecule but that do not alter the desired activity of the encoded polypeptide would result in substantially the same sequence. A nucleotide or amino acid sequence is substantially the same if the difference in that sequence from the reference parental sequence does not result in any measurable difference in the desired activity of the encoded polypeptide.

The invention provides a method for identifying a thermostable polymerase having altered fidelity. The method consists of generating a random population of polymerase mutants by mutating at least one amino acid residue of a thermostable polymerase and screening the population for one or more active polymerase mutants by genetic selection.

The generation and identification of polymerases having altered fidelity or altered catalytic activity is accomplished by first creating a population of mutant polymerases through random sequence mutagenesis of regions within the polymerase that can influence the fidelity of polymerization (Loeb, L. A., Adv. Pharmacol. 35:321-347 (1996)). The identification of active mutants is performed in vivo and is based on genetic complementation of conditional polymerase mutants under non-permissive conditions. Once identified, the active polymerases are then screened for fidelity of polynucleotide synthesis.

The methods of the invention employ a population of polymerase mutants and the screening of the polymerase mutant population to identify an active polymerase mutant. Using a population of polymerase mutants is advantageous in that a number of amino acid substitutions including single amino acid and multiple amino acid substitutions can be examined for their effect on polymerase fidelity. The use of a population of polymerase mutants increases the probability of identifying a polymerase mutant having a desired fidelity.

Screening a population of polymerase mutants has the additional advantage of alleviating the need to make predictions about the effect of specific amino acid substitutions on the activity of the polymerase. The substitution of single amino acids has limited predictability as to its effect on enzymatic activity and the effect of multiple amino acid substitutions is virtually unpredictable. The methods of the invention allow for screening a large number of polymerase mutants which can include single amino acid substitutions and multiple amino acid substitutions. In addition, using screening methods that select for active polymerase mutants has the additional advantage of eliminating inactive mutants that could complicate screening procedures that require purification of polymerase mutants to determine activity.

Moreover, the methods of the invention allow for targeting of amino acid residues adjacent to immutable or nearly immutable amino acid residues. Immutable or nearly immutable amino acid residues are residues required for activity, and those immutable residues located in the active site provide critical residues for polymerase activity. Mutating amino acid residues adjacent to these required residues provides the greatest likelihood of modulating the activity of the polymerase. Introducing random mutations at these sites increases the probability of identifying a mutant polymerase having a desired alteration in activity such as altered fidelity.

A polymerase is selected as a parent polymerase to introduce mutations for generating a library of mutants. Polymerases obtained from thermophlic organisms such as *Thermus aquaticus* have particularly desirable enzymatic characteristics due to their stability and activity at high temperatures. Thermostable polymerases are stable and retain activity at temperatures greater than about 37° C., generally greater than about 50° C., and particularly greater than about 90° C. The use of the thermostable polymerase Taq DNA polymerase I as a parent polymerase to generate polymerase mutants is disclosed herein (see Example I).

Although a specific embodiment using Taq DNA polymerase I is disclosed in the examples, the methods of the invention can similarly be applied to other thermostable polymerases other than *Thermus aquaticus* DNA polymerases. Such other polymerases include, for example, RNA polymerases from *Thermus aquaticus* and RNA and DNA polymerases from other thermostable bacteria. Using the guidance provided herein in reference to DNA polymerases, those skilled in the art can apply the teachings of the invention to the generation and identification of these other polymerases having altered fidelity of polynucleotide synthesis.

In addition to creating mutant DNA polymerases from organisms that grow at elevated temperatures, the methods of the invention can similarly be applied to non-thermostable polymerases provided that there is a selection or screen such as the genetic complementation of a conditional polymerase mutation as described herein (see Example I). Such a selection or screen of a non-thermostable polymerase can be, for example, the inducible or repressible-expression of an endogenous polymerase. Polymerases having altered fidelity can similarly be generated and selected from both prokaryotic and eukaryotic cells as well as viruses. Those skilled in the art will know how to apply the teachings described herein to the generation of polymerases having altered fidelity from such other organisms and such other cell types.

Thus, the invention provides a general method for the production of a polymerase that has an altered fidelity in DNA or RNA synthesis. The method consists of producing a population of sufficient size and diversity so as to contain at least one polymerase molecule having an altered fidelity and then screening that population to identify the polymerase having altered fidelity. The altered polymerase fidelity can be either an increase or decrease in the accuracy of DNA synthesis.

In one embodiment, the invention involves the production of a relatively large population of randomly mutagenized nucleic acids encoding a polymerase and. introduction of the population into host cells to produce a library. The mutagenized polymerase encoding nucleic acids are expressed, and the library is screened for active polymerase mutants by complementation of a temperature sensitive mutation of an endogenous polymerase. Colonies which are viable at the non-permissive temperature are those which have polymerase encoding nucleic acids which code for active mutants.

To generate a random population of polymerase mutants, a random sequence of nucleotides is substituted. for a defined target sequence of a plasmid-encoded gene that specifies a biologically active molecule. In one application of this procedure, a double-stranded oligodeoxyribonucleotide is provided by hybridizing two partially complementary oligonucleotides, one or both of which contain random sequences at specified positions. The partially double-stranded oligonucleotide is filled in by DNA polymerase, cut at restriction sites and ligated into a DNA vector. The plasmid encodes the gene for a thermo stable DNA polymerase, and the oligonucleotide is inserted in place of a portion of the gene that modulates the fidelity of DNA synthesis. After ligation, the reconstructed plasmids constitute a library of different nucleic acid sequences encoding the thermostable DNA polymerase and polymerase mutants.

As disclosed herein, a genetic screen can be used to identify active polymerase mutants having altered fidelity. The library of nucleic acid sequences encoding polymerase and polymerase mutants are transfected into a bacterial strain such as *E. coli* strain recA718 polA12, which contains a temperature sensitive mutation in DNA polymerase. Exogenous DNA polymerases have been shown to functionally substitute for *E. coli* DNA polymerase I using *E. coli* strain recA718 polA12 and to complement the observed growth defect at elevated temperature, presumably caused by the instability of the endogenous DNA polymerase I at elevated temperatures (Sweasy and Loeb, *J. Biol. Chem.* 267:1407-1410 (1992); Kim and Loeb, *Proc. Natl. Acad. Sci USA* 92:684-688 (1995)). It was unknown, however, whether a thermostable polymerase could substitute for *E. coli* DNA polymerase given the distinct and harsh environment experienced by thermophilic organisms in which enzymes must function at extremely high temperatures. As disclosed herein, wild type Taq DNA polymerase I was found to complement the growth defect of *E. coli* strain-recA718 polA12 (see Example I). Using such a complementation system, various mutant Taq DNA polymerase I mutants were identified in host bacteria that harbor plasmids encoding active thermoresistant DNA polymerases that allowed bacterial growth and colony formation at elevated (restrictive) temperatures (see Examples I and II).

The invention also provides a method for identifying a thermostable polymerase having altered fidelity. The method consists of generating a random population of polymerase mutants by mutating at least one amino acid residue in an active site O-helix of a thermostable polymerase and screening the population for one or more active polymerase mutants.

The invention additionally provides a method for identifying a thermostable polymerase having altered catalytic activity. The method consists of generating a random population of polymerase mutants by mutating at least one amino acid residue of a thermostable polymerase 10 and screening the population for one or more active polymerase mutants.

A random population of polymerase mutants is generated by mutating one or more amino acid residues in an active site O-helix target sequence of a thermostable polymerase. The O-helix has been postulated to interact with the substrate template complex (Joyce and Steitz, supra, (1994)). The O-helix has been observed in the crystal structure of *E. coli* DNA polymerase I Klenow fragment and Taq DNA polymerase (Beese et al., *Science* 260:352-355 (1993); Kim et al., *Nature* 376:612-616 (1995)}. As disclosed in Example II, random sequences were substituted for nucleotides encoding amino acids Arg659 through Tyr671 of-the O-helix of Taq DNA polymerase I to generate a random population of polymerase mutants.

Using a genetic complementation screen, a variety of active Taq DNA polymerase I mutants were identified (see Example II). Several amino acid residues were found to be immutable or nearly immutable based on the complementation assay. These immutable or nearly immutable amino acid residues in the O-helix are Arg659, Lys663, Phe667 and Tyr671. As used herein, a wild type amino acid is designated as a residue preceding the number of the amino acid position. A mutated amino acid is designated as a residue following the number of the amino acid position. These immutable or nearly immutable sites are unable to be altered and still maintain the function of the DNA polymerase. Due to their position in-the active site O-helix of Taq DNA polymerase I, these immutable or nearly immutable residues provide critical residues that are required for the activity of the polymerase.

In addition to the O-helix of a polymerase, other regions of the polymerase can be targeted for random mutagenesis to generate a library of polymerase mutants to identify polymerase mutants having altered fidelity. Those skilled in the art can determine other regions to target for mutagenesis. Such other regions can be identified, for example, by sequence homology to other polymerases, which suggests conservation of function. Conserved sequences can also be used to identify target regions for mutagenesis based on activity studies of other polymerases. Protein structural models revealing the convergence of amino acid residues at the active site of a polymerase can similarly be used to identify target regions for mutagenesis.

Alternatively, mutagenesis throughout the polymerase can be used to identify amino acid residues critical for polymerase function. Sequences containing these critical amino acid residues are target sequences for introducing random mutations to identify mutants having altered fidelity. Methods for identifying critical amino acid residues by introducing a small number of random mutations throughout a gene segment are well known to those skilled in the art and include, for example, copying by mutagenic polymerases, exposure of templates to DNA damaging agents prior to inserting into cells and replacement of regions of the DNA template with oligonucleotides containing sparsely populated random inserts. For example, a population of oligonucleotides with 91% correct substitutions and 3% of the non-complementary nucleotides at each position can be generated. Screening for polymerase mutants can be performed, for example, with the genetic complementation assay disclosed herein.

The invention also provides a method for identifying a thermostable polymerase having altered fidelity. The method consists of generating a random population of polymerase mutants by mutating one or more amino acid residues adjacent to an immutable or nearly immutable residue in an active site O-helix of a thermostable polymerase and screening the population for one or more active polymerase mutants.

In one embodiment, substitutions at amino acids 20 adjacent to immutable or nearly immutable residues are used to identify polymerase mutants having altered fidelity. The adjacent amino acid residues can be immediately adjacent in the linear sequence or can be nearby. Adjacent residues that are nearby can be as many as two amino acids away from the immutable or nearly immutable residue in the linear sequence. A nearby residue can also be nearby in the three-dimensional structure of the polymerase and can be determined from a crystallographic molecular model of a polymerase. Nearby residues are in close enough proximity to an immutable or nearly immutable residue to modulate the activity of the polymerase. Generally, nearby residues are within two amino acid residues in the linear sequence from an immutable or nearly immutable residue or are within about 5 Å of the immutable or nearly immutable residues, in particular within about 3 Å.

Substitutions involving amino acid residues adjacent to immutable or nearly immutable sites have been found to alter the fidelity of DNA synthesis (see Examples IV and V). The identified immutable or nearly immutable amino acid residues correspond to amino acid residues Arg659, Lys663, Phe667 and Tyr671 of Taq DNA polymerase I. Thus, the invention is directed to altering one or more amino acid residues adjacent to an amino acid residue corresponding to Arg659, Lys663, Phe667 or Tyr671 in Taq DNA polymerase. Amino acid residues adjacent to these immutable residues include, for example, amino acids corresponding to Arg660, Ala661, Ala662, Thr664, Ile665, Asn666, Gly668, Val669 and Leu670 in Taq DNA polymerase I. Corresponding residues in other polymerases are also included and can be identified based on sequence homology or based on corresponding amino acids in structurally similar domains as defined by a crystallographic molecular model.

The methods of the invention are also directed to altering residues immediately adjacent to the immutable or nearly immutable residues. Thus, the methods of the invention are directed to altering residues adjacent to required residues on DNA polymerases and identifying those mutations which have an effect on the fidelity of DNA synthesis.

The invention further provides methods for determining a fidelity of the active polymerase mutant. The fidelity of active polymerase mutants can be determined by several methods. The active polymerases can be, for example, screened for altered fidelity from crude extracts of bacterial cells grown from the viable colonies. Methods for determining fidelity of synthesis are disclosed herein (see Example III). In one method, a primer extension assay is used with a biased ratio of nucleoside triphosphates consisting of only three of the nucleoside triphosphates. Elongation of the primer past template positions that are complementary to the deleted nucleoside triphosphate substrate in the reaction mixture results from errors in DNA synthesis. Processivity of high fidelity polymerases will terminate when they encounter a template nucleotide complementary to the missing nucleoside triphosphate whereas the low fidelity polymerases will be more likely to misincorporate a non-complementary nucleotide. The accuracy of incorporation for the primer extension assay can be measured by physical criteria such as by determining the size or the sequence of the extension product. This method is particularly suitable for screening for low fidelity mutants since increases in chain elongation are easily and rapidly quantitated.

A second method for determining the fidelity of polymerase mutants employs a forward mutation assay. A template containing a single stranded gap in a reporter gene such as lacZ is used for the forward mutation assay. Filling in of the gapped segment is carried out by crude heat denatured bacterial extracts harboring plasmids expressing a thermostable DNA polymerase mutant. For determining low fidelity polymerase mutants, reactions are carried out in the presence of equimolar concentrations of each nucleoside triphosphate. For determining high fidelity polymerase mutants, the reaction is carried out with a biased pool of nucleoside triphosphates. Using a biased pool of nucleoside triphosphates results in incorporation of errors in the synthesized strand that are proportional to the ratio of non-complementary to complementary nucleoside triphosphates in the reaction. Therefore, the bias exaggerates the errors produced by the polymerases and facilitates the identification of high fidelity mutants. The fidelity of DNA synthesis is determined from the number of mutations produced in the reporter gene.

Procedures other than those described above for ID identifying and characterizing the fidelity of a polymerase are known in the art and can be substituted for identifying high or low fidelity mutants. Those skilled in the art can determine which procedures are appropriate depending on the needs of a particular application.

Also provided herein is an isolated thermostable polymerase mutant having altered fidelity. The polymerase mutant has one or more mutated amino acid residues in the active site O-helix of a thermostable polymerase. Additionally provided is an isolated thermostable polymerase mutant having altered fidelity. The polymerase mutant has one or more mutated amino acid residues adjacent to an immutable or nearly immutable amino acid residue in the active site O-helix of a thermostable polymerase. The mutated amino acid residue is adjacent to an amino acid residue corresponding to Arg659, Lys663, Phe667 or Tyr671 in Taq DNA polymerase.

The invention also provides an isolated thermostable polymerase mutant having altered fidelity, where the polymerase has one or more mutated amino acid residues adjacent to an amino acid residue corresponding to Arg659, Lys663, Phe667 or Tyr671 in Taq DNA polymerase and the mutant is a high fidelity mutant.

Using the methods of the invention, a number of mutants have been identified as having high fidelity of DNA synthesis. For example, polymerases having one or more single-base substitutions adjacent to Arg659, Lys663, Phe667, and Tyr671 in the nucleotide sequence of Taq DNA polymerase I have been identified. Specific examples of these high fidelity mutants include, for example, polymerases having the single substitutions Asn666Asp, Asn666Ile, Ile665Leu, Leu670Val, Arg660Tyr Arg660Ser, Gly668Arg, Arg660Lys, Gly668Ser and Gly668Gln; polymerases having the double substitutions consisting of Thr664Ile together with Asn666Asp, and Ala661Ser together with Val669Leu; as well as polymerases having the triple substitutions consisting of Thr664Pro, Ile665Val together with Asn666Tyr, and Ala661Glu, Ile665Thr together with Phe667Leu. Additional high fidelity mutants include, for example, Phe667Leu and Phe667Tyr.

The invention provides a high fidelity polymerase mutant having one or more amino acid substitutions selected from the group consisting of Phe667Leu; Asn666Asp; Asn666Ile; Ile665Leu; Leu670Val; Arg660Tyr; Arg660Ser; Gly668Arg; Arg660Lys; Gly668Ser; Gly668Gln; Thr664Ile and Asn666Asp; Ala661Ser and Val669Leu; Ala661Glu, Ile665Thr, and Phe667Leu; and Thr664Pro, Ile665Val and Asn666Tyr. The polymerase mutant Phe667Tyr has been previously described and is excluded from the compositions of the invention.

The invention also provides an isolated thermostable polymerase mutant having altered fidelity, where the polymerase has one or more mutated amino acid residues adjacent to an amino acid residue corresponding to Arg659, Lys663, Phe667 or Tyr671 in Taq DNA polymerase and the mutant is a low fidelity mutant. The invention additionally provides a low fidelity polymerase mutant having one or more amino acid substitutions selected from the group consisting of Ala661Glu; Ala661Pro; Thr664Pro; Thr664Asn; Thr664Arg; Asn666Val; Thr664Pro and Val669Ile; Arg660Pro and Leu670Thr; Arg660Trp and Thr664Lys; Ala662Gly and Thr664Asn; AlaG61Gly and Asn666Ile; Ala661Pro and Asn666Ile; and Ala661Ser, Ala662Gly, Thr664Ser and Asn666Ile.

Low fidelity mutant DNA polymerases include mutations involving substitutions at Ala661, Thr664, Asn666, and Leu670. Specific examples of low fidelity mutants include, for example, polymerases having the single substitutions Ala661Glu, Ala661Pro, Thr664Pro, Thr664Asn, Thr664Arg and Asn666Val; polymerases having the double substitutions consisting of Thr664Pro together with Val669Ile, Arg660Pro together with Leu670Thr, Arg660Trp together with Thr664Lys, Ala664Gly together with Thr664Asn, Ala661Gly together with Asn666Ile, and Ala661Pro together with Asn666Ile; as well as polymerases having four substitutions consisting of Ala661Ser, Ala662Gly, Thr664Ser together with Asn666Ile.

For both the high fidelity and the low fidelity mutations described above, the invention provides polymerases other than Taq DNA polymerase having mutations at corresponding positions. In particular, the invention provides thermostable polymerases other than Taq DNA polymerase that have mutations at corresponding positions and that have altered fidelity. Those skilled in the art can determine corresponding positions based on sequence homology between the polymerases.

The invention also provides an isolated nucleic acid molecule encoding a polymerase mutant having high fidelity. The nucleic acid molecule contains a nucleotide sequence encoding substantially an amino acid sequence of Taq DNA polymerase I having one or more amino acid substitutions selected from the group consisting of Phe667Leu; Asn666Asp; Asn666Ile; Ile665Leu; Leu670Val; Arg660Tyr; Phe667Tyr; Arg660Ser; Gly668Arg; Arg660Lys; Gly668Ser; Gly668Gln; Thr664Ile and Asn666Asp; Ala661Ser and Val669Leu; Ala661Glu, Ille665Thr, and Phe667Leu; and Thr664Pro, Ile665Val and Asn666Tyr.

Additionally provided is an isolated nucleic acid molecule encoding a polymerase mutant having low fidelity. The nucleic acid molecule contains a nucleotide sequence encoding substantially an amino acid sequence of Taq DNA polymerase I having a substitution of one or more amino acids selected from the group consisting of Ala661, Thr664, Asn666 and Leu670. The invention also provides a polymerase mutant having one or more amino acid substitutions selected from the group consisting of Ala661Glu; Ala661Pro; Thr664Pro; Thr664Asn; Thr664Arg; Asn666Val; Thr664Pro and Val669Ile; Arg660Pro and Leu670Thr; Arg660Trp and Thr664Lys; Ala664Gly and Thr664Asn; Ala661Gly and Asn666Ile; Ala661Pro and Asn666Ile; and Ala661Ser, Ala662Gly, Thr664Ser and Asn666Ile.

The invention also provides methods for the identification of one or more mutations in a gene using the high fidelity mutant DNA polymerases of the invention. For example, the use of a high fidelity mutant to amplify a gene of interest gives greater confidence that the amplified sequence will more accurately reflect the actual sequence in the sample and minimizes the introduction of artifactual mutations during amplification of the gene. The higher accuracy of gene amplification provided by a high fidelity mutant also improves the identification of genetic mutations due to the increased confidence that observed mutations are more likely to reflect genetic mutations in the sample rather than artifactual mutations introduced during amplification.

Additionally, the invention provides methods for identifying one or more mutations in a gene by amplifying the gene using a high fidelity polymerase mutant under conditions which allow polymerase chain reaction amplification. The gene is amplified by exposing the strands of the gene to repeated cycles of denaturing, annealing and elongation to produce an amplified gene product. Methods for amplifying genes using PCR are well known to those skilled in the art and include those described previously in *PCR Primer. A Laboratory Manual*, Dieffenbach and Dveksler, eds., Cold Spring Harbor Press, Plainview, N.Y. (1995). The presence or absence of one or more mutations in the gene can be determined by sequencing the amplified product using methods well known to those skilled in the art.

The invention provides methods for accurately copying repetitive nucleotide sequences by amplifying the repetitive nucleotide sequence using a high fidelity polymerase mutant. The repetitive nucleotide sequence can be in a gene or in a microsatellite between genes. The methods of amplifying, the repetitive nucleotide sequences are carried out under conditions which allow PCR amplification with repeated cycles of denaturing, annealing and elongation as described above.

The high fidelity mutants of the invention are advantageous for copying repetitive nucleotide sequences such as repetitive DNA because polymerases found in nature undergo slippage when copying DNA containing repetitive sequences. Therefore when polymerases found in nature are used, the amplification products of a nucleotide sequence containing a repetitive sequence do not accurately reflect the size or sequence of a DNA sequence in a sample. However, the use of a high fidelity polymerase mutant greatly increases the accuracy of an amplification product to reflect the actual size and sequence of the repetitive DNA sequence in the sample. Repetitive DNA can be found in microsatellites, which contain multiple repetitive nucleotide sequences and are dispersed throughout the genome. These repetitive di-, tri- and tetranucleotides are frequently, but not invariably, located between genes.

The invention also provides a method for determining an inherited mutation by amplifying a gene using a high fidelity polymerase mutant. Such an inherited mutation can be correlated with a genetic disease, thereby allowing diagnosis of the genetic disease. The invention additionally provides methods for diagnosing a genetic disease by amplifying a gene using a high fidelity polymerase mutant. A genetic disease is one in which a disease is caused by a genetic mutation in a coding or non-coding region of DNA. Such a genetic mutation can be a somatic mutation or a germline mutation. The methods of the invention can be used to diagnose any genetic disease using high fidelity polymerase mutants. Such genetic diseases can involve point mutations, insertions and deletions.

The methods of the invention employ high fidelity polymerase mutants and can similarly be used to diagnose genetic diseases involving repetitive DNA. In one embodiment, the genetic disease involves mutations in a microsatellite or repetitive DNA. Microsatellites are relatively stable in normal cells but are found to be unstable and to vary in length in some forms of hereditary and non-hereditary cancer, including hereditary nonpolyposis colorectal cancer (HNPCC), other cancers that arise in HNPCC families, Muir-Tone syndrome and small-cell lung cancer (Loeb, *Cancer Res.* 54:5059-5063 (1994); Brentnall, *Am. J. Pathol.* 147:561-563 (1995); Honchel et al., *Semin. Cell Biol.* 6:45-52 (1995); Eshleman and Markowitz, *Curr. Opin. Oncol.* 7:83-89 (1995)). Microsatellite instability appears to be confined to tumors and is not present in normal tissues of affected individuals.

The accuracy of amplification products of repetitive DNA sequences provided by the high fidelity mutants of the invention can be used to diagnose diseases involving mutations in repetitive DNA sequences. For example, with tumor samples, the accurate amplification of repetitive DNA sequences can be used to diagnose those cancers involving variable length in microsatellite DNA. Since microsatellite instability appears to be confined to tumors, amplification of repetitive DNA using the high fidelity mutants of the invention can additionally be applied to determining the prognosis or extent of disease of a cancer patient, evaluating outcomes of therapy, staging tumors and determining tumor status. High fidelity mutants of the invention can also be applied to amplify DNA in blood samples to identify circulating cells containing microsatellite instability as an indicator of a cancerous state.

Other genetic diseases also involve repetitive DNA sequences, in particular, unstable triplet repeats. These unstable triplet repeat diseases involve increasing lengths of triplet repeat regions, ranging from ~50 repeats in normal individuals, ~200 repeats in carriers to ~2000 repeats in affected individuals. Such unstable triplet repeat diseases include, for example, fragile X syndrome, spinal and bulbar muscular atrophy, myotonic dystrophy, Huntington's disease, spinocereballar ataxia type 1, fragile X E mild mental retardation and dentatorubral pallidoluyysian atrophy (Monckton and Caskey, *Circulation* 91:513-520 (1995)). The diagnosis of unstable triplet repeat diseases is particularly valuable since the onset of symptoms can occur later in some diseases and the severity of the symptoms of some diseases can be correlated with the size of the extended triplet repeat region. Thus, amplification of these triplet repeat regions to more accurately reflect the actual size of the triplet repeat in the individual provides more accurate diagnosis and prognosis of the disease. Amplification of the large expanded regions associated with triplet repeat diseases can be carried out using low fidelity polymerase mutants of the invention since low fidelity polymerase mutants would be more likely to copy through very long stretches of repetitive nucleotide sequences.

One method for identifying a genetic disease involves utilization of primers that hybridize to specific genes. The primers contain 3'-terminal nucleotides complementary to the corresponding nucleotide in the mutant but not to the wild type gene. The mismatched primer is used to extend the primer template in the presence of a high fidelity mutant polymerase. The presence of an extension product is indicative of a mutant gene.

The mismatch PCR method is based on the fact that a PCR primer that is not complementary to the template at the 3' end is an inefficient substrate for polymerases such as Taq DNA polymerase I. Wild type Taq DNA polymerase will occasionally misextend a mismatched primer, resulting in a false positive in an assay for a gene mutation. For example, a mutant gene with a rare TT mutation would be difficult to specifically amplify out of a pool of DNA molecules containing a wild type CC at the position of the TT mutant because wild type Taq DNA polymerase would occasionally misextend the wild type gene using the mismatched primer. In contrast, a high fidelity polymerase would not extend the mismatched primer. The products of a high fidelity polymerase in the mismatch PCR assay would therefore correspond to the mutant gene and would have fewer false positives than that observed with wild type Taq DNA polymerase. Thus, the more discriminating assay based on the use of high fidelity polymerases results in a better assay for detecting somatic mutations. The use of high fidelity mutants in such a mismatch-PCR based assay is disclosed herein (see Example V).

The invention also provides a method for randomly mutagenizing a gene by amplifying the gene using the low fidelity polymerase mutants of the invention. The low fidelity polymerase mutants exhibit an efficiency of accurate base incorporation that is less than that of wild type polymerases. The efficiency of the low fidelity polymerase mutant is about 50% or more, generally 10% or more, and particularly 1% or more than that of a wild type polymerase. These low fidelity polymerase mutants would therefore exhibit between 2-fold to 100-fold lower fidelity than wild type polymerase. The introduction of mutations into specific genes using low fidelity polymerase mutants of the invention is useful for determining the effects of mutations on the function of those gene products.

It is understood that modifications which do not substantially affect the activity of the various embodiments of this invention are also included within the definition of the invention provided herein. Accordingly, the following examples are intended to illustrate but not limit the present invention.

EXAMPLE I

Random Sequence Mutagenesis and Identification of Active Tap DNA Polymerase Mutants This example demonstrates random nucleotide sequence mutagenesis of a polymerase target sequence and identification of active polymerase mutants.

Random sequence mutagenesis was used to introduce mutations into the O-helix of Taq DNA polymerase. Briefly, the Tag DNA polymerase I gene was obtained from the bacterial chromosome by cloning in pKK223-3 (Pharmacia Biotech, Piscataway, N.J.). A 3.2-kb fragment containing the Taq DNA polymerase I gene, including the 5'-3' exonuclease domain and the tac promoter region, was further transferred into the SalI site of pHSG576 (pTacTaq). The Taq DNA polymerase I gene was sequenced to confirm wild type sequence except for the lack of the N-terminal three amino acids.

A vector containing a nonfunctional insert within the Taq DNA polymerase I gene was constructed and subsequently replaced with an oligonucleotide containing the random sequence to avoid contamination with incompletely cut vectors. To generate the nonfunctional vector, a SacII site was produced using site-directed mutagenesis by changing 2070C to G using a synthetic oligomer, 5'-GGG TCC ACG GCC TCC CGC GGG ACG CCG AAC ATC CAG CTG (SEQ ID NO:3) (SacII-2) and the single-stranded plasmid pFC85 (Kunkel, *Proc. Natl. Acad. Sci. USA* 82:488-492 (1985)). The BstX1-NheI fragment that carries the SacII site was substituted for the corresponding fragment in pTacTaq (pTacTaqSac). A SacII-NheI fragment in pTacTaqSac was further replaced with the synthetic oligomer 5'-GGA CTG CAT ATG ACT G (SEQ ID NO:4) (DUM-U) hybridized with 5'-CTA GCA GTC ATA TGC AGT CCG C (SEQ ID NO:5) (DUM-D) to create the nonfunctional vector (Dube et al., *Biochemistry* 30:11760-11767 (1991)).

Oligonucleotides containing 9% random sequence, 20 in which each nucleotide indicated in parentheses was 91% wild type nucleotide and 3% each of the other three nucleotides, were—synthesized by Keystone Laboratories (Menlo Park, Calif.): O+9 RANDOM is 5'-CGG GAG GCC GTG GAC CCC CTG ATG (CGC CGG GCG-GCC AAG ACC ATC AAC TTC GGG GTC CTC TAC) GGC ATG TCG GCC CAC CG (SEQ ID NO:6); O-0 RANDOM is 5'-TGG CTA GCT CCT GGG AGA GGC GGT GGG CCG ACA TGC C (SEQ ID NO:7). The 17 nucleotide sequences at the 3' ends of the two oligonucleotides are complementary. Equimolar amounts of these oligonucleotides (20 pmol) were mixed, hybridized, and extended by five cycles of PCR reaction (94° C. for 30 sec, 57° C. for 30 sec, and 72° C. for 30 sec) in a 100 pl reaction mixture containing 10 mM Tris-HCl (ph 8.3), 50 mM KCl, 1.5 mM MgCl2, 0.001% gelatin, 50 µM dNTPs, and 2.5 units of Taq DNA polymerase I. This PCR product (10 µl) was further amplified 25 cycles with 20 pmol of O(+) PRIMER (5'-TTC GGC GTC CCG CGG GAG GCC GTG GAC CCC CT) (SEQ ID NO:8) and 20 pmol of O(−) PRIMER (5'-GTA AGG GAT GGC TAG CTC CTG GGA) (SEQ ID NO:9) under the same conditions. The amplified product was purified by phenol/chloroform extraction followed by ethanol precipitation and digestion with the restriction enzymes, SacII and NheI, at 37° C. for 30 min in 50 mM Tris-HCl (pH 7.9), 50 mM NaCl, 10 mM MgCl₂ and 1 mM dithiothreitol. The restriction fragment containing the random sequence was purified by phenol/chloroform extraction, ethanol precipitation, and filtration using a Microcon 30 filter (Amicon, Beverly, Mass.). For the totally random library, five oligonucleotides (80-mers), each having totally random sequence at one of the codons 659, 660, 663, 667 or 668, were combined in equal amounts and hybridized to O-0 RANDOM. After extension and digestion with endonucleases, the combined products were purified and processed as above.

A random library of Tag DNA polymerase genes containing randomized nucleotide sequence corresponding to the O-helix was generated by digesting the vector containing the nonfunctional insert with NheI and SacII restriction endonucleases. The large DNA fragment was isolated by electrophoresis in a 0.8% agarose gel and purified by using Gen- CleanII (Bio101, Vista, Calif.). This large fragment, lacking the nonfunctional insert, was ligated with an oligonucleotide containing randomized sequence by incubating overnight at 16° C. with T4 DNA ligase. The ligation mixture was then used to transform DH5α by electroporation according to Bio-Rad (Hercules, Calif.). After electroporation, 1 ml of SOC (2% hactotryptone/0.5% yeast extract/10 mM NaCl/2.5 mM KCl/10 mM $MgCl_2$/10 mM $MgSO_4$/20 mM glucose) was added and incubation continued for 1 h at 37° C. An aliquot was plated on 2×YT (16 g/liter tryptone, 10 g/liter yeast extract, 5 g/liter NaCl, pH 7.3) containing 30 pg/ml chloramphenicol to determine the total number of transformants, and the remainder was inoculated into 500 ml of 2×YT containing 30 µg/ml chloramphenicol and cultured at 37° C. overnight. Plasmids (random library vector) were purified and used for transformation of recA718 polA12 strain.

For genetic complementation to determine active polymerase mutants, E. coli recA719 polA12 cells (SC18-12 E. coil B/r strain, which has the genotype recA718 polA12 uvrA155 trpE65 lon-11 sulA1) were transformed with plasmids pHSG576 or pTacTaq by electroporation (Bio-Rad Genepulser, 2 kV, 25 µFD, 400 Ω) (Sweasy and Loeb, supra, (1992); Sweasy and Loeb, Proc. Natl. Acad. Sci. USA 90:4626-4630 (1993); Witkin and Roegner-Maniscalo, J. Bacteriol. 174:4166-4168 (1992)). Thereafter, 1 ml of nutrient broth (NB) (8 g/liter) containing NaCl (4 g/liter) and 1 mM isopropyl β-D-thiogalactoside (IPTG) was added and the mixture was incubated for 1 h at 37° C. The transformed cells were plated on nutrient agar plates (containing 23 g/liter Difco nutrient agar, 5 g/liter NaCl, 30 µg/ml chloramphenicol, 12.5 µg/ml tetracycline and 1 mM IPTG) and grown at 30° C. overnight. Single colonies were transferred to NB for growth to logarithmic phase at 30° C. Thereafter, ~10 µl ($10^4$ cells) was introduced at the center of an agar plate, and the inoculation loop was gradually moved from the center to the periphery as the plate was rotated. Duplicate plates were incubated at 30° C. or 37° C. for 30 h. To determine complementation efficiency by Taq DNA polymerase I and to isolate mutants, cultures of the recA718 polA12 strain harboring either pHSG576 or Taq DNA polymerase I were diluted with NB medium and plated (~500 colonies per plate). Duplicate plates were incubated at 30° C. or 37° C., and visible colonies were counted after a 30 h incubation. Complementation was verified by a second round of electroporation and colony formation at the nonpermissive temperature. Cell-free extracts were prepared from selected colonies obtained at the restrictive temperature and assayed to confirm that they contained a temperature-resistant DNA polymerase activity (Lawyer et al., J. Biol. Chem. 264:6427-6437 (1989)).

Wild type Tag DNA polymerase I was tested for its ability to complement a temperature sensitive polymerase contained in the E. coli strain recA718 polA12, which is unable to grow at 37° C. in rich media at low cell density (Witkin and Roegner-Maniscalo, 1992, supra). The temperature sensitive phenotype of E. coli strain recA718 polA12 was complemented by transformation with the pTacTaq plasmid encoding wild type Taq DNA polymerase I as indicated by growth at 37° C. Therefore, this E. coli strain containing a temperature sensitive polymerase provides a good model system for testing Taq DNA polymerase I mutants.

To evaluate the involvement of different amino acid residues in catalysis by Taq DNA polymerase I, random sequences were substituted for nucleotides encoding a portion of the substrate binding site of Taq DNA polymerase I (O-helix, amino acids Arg659 through Tyr671). The substituted stretch was 39 nucleotides long with 9% randomization. At each position the proportion of the wild type residue was 91% and the other 3 nucleotides were present in equal amounts (3% each).

A library of 50,000 independent mutants was obtained. The number of colonies obtained at 37° C. was 11.8% of that obtained at 30° C. Therefore, screening a randomized library using, E. coli strain recA718 polA12 provided approximately 5900 colonies containing active Taq DNA polymerase and potential polymerase mutants.

These results show that a randomized library can be used to generate a population of polymerase mutants. These results also show the identification of active Taq DNA polymerase I mutants by screening for active polymerase mutants using genetic selection.

EXAMPLE II

Identification of Tag DNA Polymerase I Mutants and Immutable or Nearly Immutable Amino Acid Residues This example describes the identification Taq DNA polymerase I mutants generated by a randomized library and the identification of immutable or nearly immutable amino acid residues.

The active Taq DNA polymerase I mutants identified by the screen described in Example I were further characterized. The entire random nucleotide-containing insert was sequenced from a total of 234 plasmids obtained at 37° C. (positively selected), 16 plasmids obtained at 30° C. (nonselected) and 29 plasmids obtained at 30° C., which failed to grow at 37° C. (negatively selected). All substitutions were in the randomized nucleotides except for 12 clones.

Among the 230 positive plasmids, 168 contained silent mutations in one or more codons. At the amino Among the 230 positive plasmids, 168 contained silent mutations in one or more codons. At the amino acid level, 106 encoded the wild type residue and 124 encoded substitutions, in accord with the expected distribution in the plasmid population. Of the 124 plasmids with amino acid changes, 40 were unique mutants obtained just once. The remaining 84 plasmids represented 21 different mutants. At least 79% of those encoding the same amino acid substitutions were independently derived since they contained different silent mutations in other codons. In total, 61 different amino acid sequences were obtained that complemented the temperature-sensitive phenotype of the recA718 polA12 host.

Figure 2B:
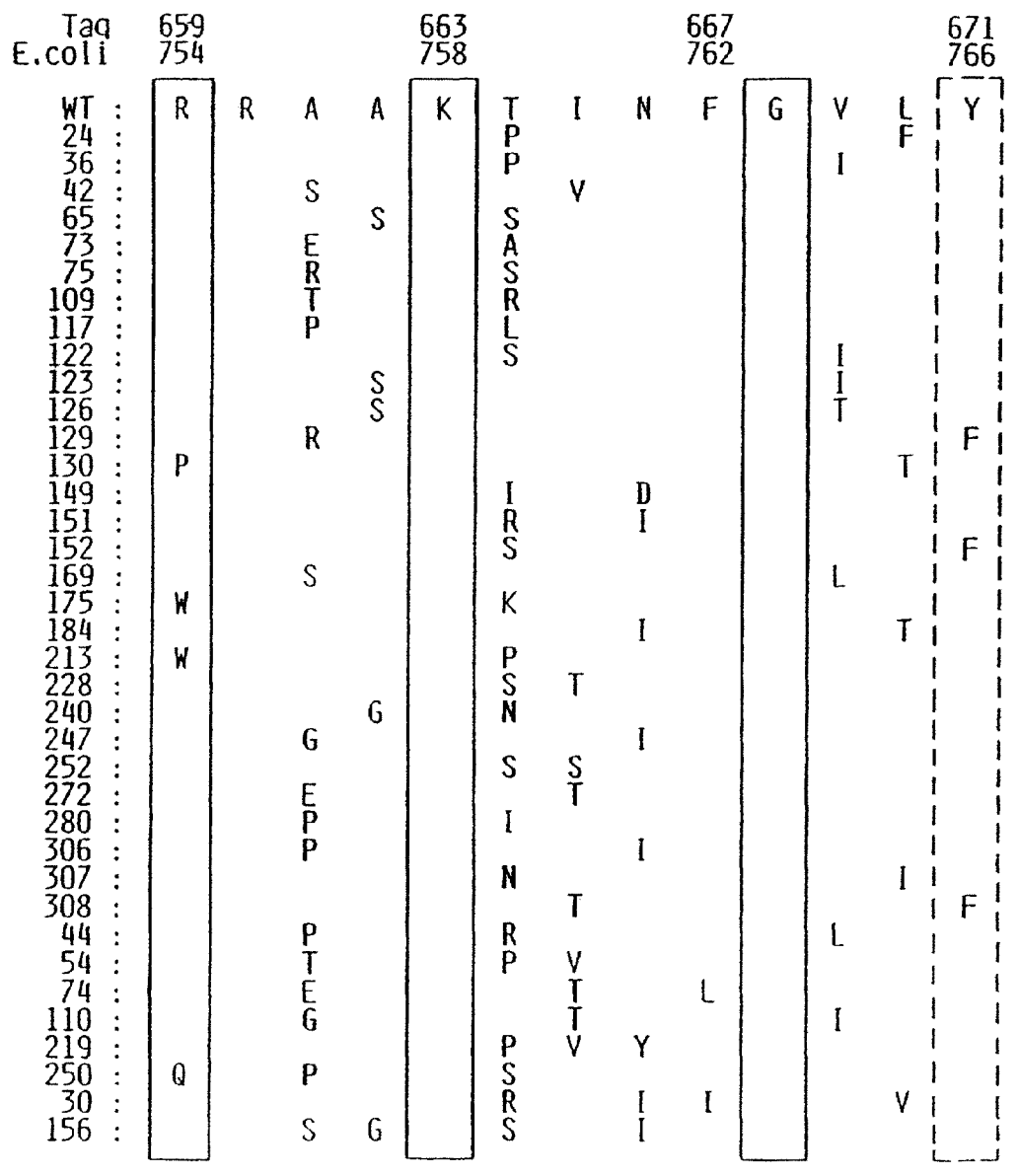

A compilation of the amino acid substitutions found in Taq DNA polymerase I is shown in FIG. 2. Solid boxes indicate the amino acid residues for which no substitutions were detected. Dashed boxes mark the amino acid positions where only conservative substitutions were found. The amino acid positions of Taq DNA polymerase I and corresponding positions of E. coli DNA polymerase I are indicated at the top. WT represents the wild type sequence-and randomized amino acids are written in boldface type. The amino acids that have not been found in the DNA polymerase I family are outlined (Braithwaite and Ito, Nucleic Acids Res. 21:787-802 (1993)). Panel A shows single mutations selected from the 9% library lsted under the wild type amino acids. Panel 8 shows the sequence of each multiply substituted mutant selected from the 9% library. Panel C shows mutations selected from the totally random library.

The distribution of single amino acid substitutions among the active mutants was not random (see FIG. 2A). For example, numerous diverse substitutions were observed at Ala661 and Thr664. In contrast, no substitutions were detected at five positions (Arg659, Arg660, Lys663, Phe667 and Gly668). This uneven distribution of replacements is unlikely to be the result of a bias in the nucleotide composition of the random insert since sequencing of both the nonselected and negatively selected plasmids revealed multiple nucleotide substitutions at each of the targeted positions and because silent mutations were detected at each of these positions in the selected clones.

A nonrandom distribution of substitutions was also observed among active mutants containing multiple substitutions (see FIG. 2B). Again, Ala661 and Thr664 were replaced with a variety of residues. However, no amino acid substitutions were observed in place of Arg659, Lys663 and Gly668, even though different silent nucleotide substitutions were found at each of these positions. A comparison of FIG. 2A and B shows that substitutions at Arg660 and Phe667 occur only in the presence of substitutions at other positions. In addition to the mutants containing multiple substitutions shown in FIG. 2B, two additional triple mutants were also found: mutant 44, with Ala661Pro, Thr664Arg, and Val669Leu; and mutant 54, with Ala661Thr, Thr664Pro and Ile665Val.

The partially substituted library (9%) does not provide a vigorous test of the immutability of specific codons. Only 0.07% of sequences at each codon would be expected to contain nucleotide substitutions at all three positions. To further probe the mutability of specific amino acid residues, a second library was constructed that contained totally random substitutions at a limited number of designated codons. In this library, nucleotides encoding each of the five amino acids Arg659, Arg660, Lys663, Phe667 and Gly668 were randomized. These were amino acid positions that did not yield single substitutions in the 9% random library (FIG. 2A). Approximately 1300 transformants, which is 4 times more than the number required for each possible substitution at each of the target codons, were screened. At the nonpermissive temperature, 113 colonies were obtained, 84 of which contained codons that encoded the wild type amino acid sequence. Most of the amino acid substitutions occurred in place of Arg660 or Gly668.

Again, Arg659 and Lys663 were completely conserved, with 16 and 5 silent mutations scored at these codons, respectively. The expected number of silent mutations were 21 and 4.2, respectively, assuming that the 5 randomized oligomers that comprised the library were mixed in equimolar proportions. These numbers show that the oligomers were roughly equally represented in the library and that sufficient mutants were sampled, to conclude that Arg659 and Lys663 are immutable in these genetic complementation experiments (P<0.05 for Met and Trp, P<0.01 for all other substitutions). Only Tyr substituted for Phe at position 667 (FIG. 2C), and six silent mutations were scored for this codon. An additional mutant obtained with the totally randomized library but not shown in FIG. 2 is mutant 601, with double substitutions Ile665Asn and Val669Ile.

These results show that generating a random library and screening by genetic complementation provided a number of active Taq DNA polymerase I mutants. These results also show that amino acid residues Arg659 and Lys663 were found to be immutable and Phe667 and Tyr671 were found to tolerate only conservative substitutions.

EXAMPLE III

Determination of the Fidelity of Active Tap DNA Polymerase I Mutants

This example describes methods of determining the fidelity of active Taq DNA polymerase I mutants. Two types of assays are useful for determining the fidelity of active polymerase mutants, a primer extension assay and a forward mutation assay.

Crude extracts were used to determine the fidelity of polymerase mutants. A single colony of $E.$ $coli$ DH5α (F, φ80dlacZΔM15, Δ(lacZYA-argF) U169, deoR, recA1, endA1, phoA, hsdR17($r_k$-$m_k^+$), supE44, A-, λ⁻, thi-1, gyrA96, relA1) carrying wild type or mutant Taq DNA polymerase I was inoculated into 40 ml of 2×YT (16 g/liter tryptone, 10 g/liter yeast extract, 5 g/liter NaCl, pH 7.3) containing 30 mg/liter chloramphenicol. After incubation at 37° C. overnight with vigorous shaking, an equal amount of fresh medium with 0.5 mM IPTG was added, and incubation was continued for 4 h. Cells were harvested, washed once with TE buffer (10 mM Tris-HCl, pH 8.0, 1 mM EDTA) and suspended in 100 µl of buffer A (50 mM Tris-HCl, pH 8.0, 2.4 mM phenylmethylsulfonyl fluoride, 1 mM dithiothreitol, 0.5 mg/liter leupeptin, 1 mM EDTA, 250 mM KCl). Bacteria were lysed by incubating with lysozyme (0.2 mg/ml) at 0° C. for 2 h. The lysate was centrifuged at 15,000 rpm (Sorvall, SA-600 rotor) (DuPont, Newtown, Conn.) for 15 min, and the supernatant solution was incubated at 72° C. for 20 min. Insoluble material was removed by centrifugation.

Polymerases were purified as described previously with some modifications (Lawyer et al., $PCR$ $Methods$ $Application$ 2:275-287 (1993). Briefly, a single colony of $E.$ $coli$ DH5α carrying wild type or mutant Taq DNA polymerase I was inoculated into 10 ml of 2×YT. Two ml of the inoculum was immediately added to each of 5 bottles containing 1 liter of 2×YT with 30 mg/liter chloramphenicol. After overnight incubation at 37° C. with vigorous shaking, 1 liter of 2×YT containing 30 mg/liter chloramphenicol and 0.5 mM IPTG was added, and incubation was continued for 4 h. Cells were harvested, washed once with TE buffer and suspended in 100 ml buffer A. Bacteria were lysed by incubating with lysozyme (0.2 mg/ml) at 0° C. for 2 h and then sonicating on ice for 45 sec by using a micro-tip probe (Sonifier, Branson Sonic Power, Danbury, Conn.).

The lysate was centrifuged at 15,000 rpm (Sorvall, SA-600 rotor) for 15 min, and the supernatant solution was incubated at 72° C. for 20 min. Insoluble material was removed by centrifugation. Ammonium sulfate (0.2 M) and Polymin P (0.6%) were added and the suspension was held on ice for 1 h. After removal of the precipitate by centrifugation and filtration through a Costar 8310 filter, the filtrate was applied to a 3×8-cm-phenyl-SEPHAROSE HP (Pharmacia Biotech) column equilibrated with buffer A containing 0.2 M ammonium sulfate and 0.01% Triton-X-100. The column was washed with the same buffer (300 ml) and activity was eluted with buffer B (TE buffer containing 0.01% Triton X-100 and 50 mM KCl). The eluate (100 ml) was dialyzed overnight against 4 liters of buffer B and loaded onto a 0.8×8-cm heparin-SEPHAROSE CL6B (Pharmacia Biotech) column equilibrated with buffer B. After washing with buffer B (50 ml), activity was eluted in a 30 ml linear gradient of 50-500 mM KCl in TE buffer containing 0.01% Triton X-100. Active fractions were collected, dialyzed against 50 mM Tris-HCl (pH 8.0) containing 50 mM KCl and 50% glycerol, and stored at −80° C.

To confirm and quantitate the presence of polymerase activity, crude extracts or purified enzyme was incubated at 72° C. for 5 min in 50 mM Tris-HCl (pH 8.0), 2 mM MgCl2, 100 µM each dATP, dGTP, dCTP and dTTP, 0.2 µCi of ($^3$H) dATP and 200 pg/ml activated calf thymus DNA. Incorporation of radioactivity into an acid-insoluble product was measured according to Battula and Loeb ($J.$ $Biol.$ $Chem.$ 249:

4086-4093 (1974). One unit represents incorporation of 10 nmol of dNMP in 1 h, corresponding to 0.1 unit as defined by Perkin-Elmer.

For the primer extension assay, the 14-mer primer 5'-CGCGCCGAATTCCC (SEQ ID NO:10) was $^{32}$P-labeled at the 5' end by incubation with ($\gamma$-$^{32}$P)ATP and T4 polynucleotide kinase and annealed to an equimolar amount of the template 46-mer 5'g-GCGCGGAAGCTTGGCTGCA-GAATATTGCTAGCGGGAATTCGGCGCG (SEQ ID NO:11). Heat-inactivated *E. coli* extracts containing 0.3-1 unit of wild type or mutant Taq DNA polymerases were incubated at 45° C. for 60 min in 50 mM Tris-HCL (pH 8.0), 2 mM MgCl$_2$, 50 mM KCl, 20:M each dATP, dGTP, dCTP and dTTP and 1.4 ng of the annealed template primer. A set of four additional reactions, each lacking a different dNTP, was carried out for each polymerase. Purified enzyme (1 unit) was incubated for the times indicated under the same conditions as for crude extracts. After electrophoresis in a 14% polyacryiamide gel containing 8M urea, reaction products were analyzed by autoradiography. Extension was quantified by using an NIH imaging program (see http//www.nih.gov/).

For the forward mutation assay, the non-coding strand of the lacZ∀ gene contained in 200 ng of gapped M13mp2 DNA was copied by using 5 units of wild type or mutant Taq DNA polymerase I in a reaction mixture containing 50 mM Tris-HCl (pH 8.0), 2 mM MgCl$_2$ and 50 mM KCl (Feig et al. *Proc. Natl. Acad. Sci. USA* 91:6609-6613 (1994)). For determining low fidelity polymerase mutants, the reaction included 20:M each dNTP. For determining high fidelity polymerase mutants, the reaction was carried out with biased dNTP pools containing 0.5 mM of one dNTP and 20 mM of each of the other three dNTPs. For example, the reaction could contain 0.5 mM dATP and 20 mM each of dGTP, dCTP and dTTP. After incubation at 72° C. for 5 min, the DNA was transfected into host *E. coli* and the plaques were scored for white and pale blue mutant plaques (Tindall et al., *Genetics* 118:551-560 (1988)).

These results show that the fidelity of active Taq DNA polymerase mutants can be determined using a primer extension assay and a forward mutation assay.

EXAMPLE IV

Identification of Low Fidelity Taq DNA Polymerase I—Mutants

This example shows the identification of low fidelity Taq DNA polymerase I mutants.

The active Taq DNA polymerase I mutants identified in Example II were assayed by the methods described in Example III to identify low fidelity mutants. Screening for activity was carried out on 67 of 75 sequenced mutants, including all 38 with single amino acid substitutions described in FIG. 2. Plasmids encoding the mutant polymerases were cloned, purified and grown in *E. coli*, and host cells were analyzed for expression of Taq DNA polymerase I by measuring the activity of crude extracts. *E. coli* DNA polymerases and nucleases were inactivated by heating at 72° C. for 20 min. The ability of heat-treated extracts to elongate primers in the absence of a complete complement of four dNTPs was then determined using a set of five reactions. One reaction contained all four complementary nucleoside triphosphates while each of the others lacked a different dNTP ("minus conditions"). Elongation in the minus reactions is limited by the rate of misincorporation at template positions complementary to the missing dNTP.

A primer extension assay was performed on wild type Taq DNA polymerase I and several mutants, revealing that several mutants had elongation patterns that differed from wild type Taq DNA polymerase. In the presence of all four dNTPs, every extract examined extended more than 90% of the hybridized primer to a product of length similar to that of the template. In the minus reactions, wild type Taq DNA polymerase I extended 48-60% of the primer up to, but not opposite, the first template position complementary to the missing dNTP. The remaining primer was terminated opposite the missing dNTP, presumably by incorporation of a single non-complementary nucleotide, or was terminated further downstream, presumably by extension of the mispaired primer terminus. A variety of elongation patterns was observed for the 67 mutants. Thirteen mutants extended more of the primer and/or synthesized a greater proportion of longer products than the wild type enzyme in three or four of the minus reactions. For example, mutant 2 formed full-length products in reactions lacking dGTP or dTTP. This increased extension presumably reflects increased incorporation and/or extension of non-complementary nucleotides. Other mutants extended less of the primer or synthesized shorter products than the wild type enzyme, for example, mutant 5. In several cases, different amino acid substitutions at the same position either increased or decreased extension in comparable minus reactions.

A compilation of amino acid replacements in the 13 mutants that displayed increased extension in at least three of the minus reactions is shown in Table I.

TABLE I

Low Fidelity Mutants of Taq DNA Polymerase I Identified in the Primer Extension Screen

| WT | 659 R | R | A | A | 663 K | T | I | N | 667 F | G | V | L | 671 Y |
|---|---|---|---|---|---|---|---|---|---|---|---|---|---|
| 29 | | | E | | | | | | | | | | |
| 36 | | | | | P | | | | | | I | | |
| 40 | | | P | | | | | | | | | | |
| 45 | | | | | P | | | | | | | | |
| 53 | | | | | N | | | | | | | | |
| 130 | | P | | | | | | | | | | | T |
| 156 | | | S | G | S | | I | | | | | | |
| 175 | | W | | | K | | | | | | | | |
| 206 | | | | | R | | | | | | | | |
| 240 | | | | G | N | | | | | | | | |
| 247 | | G | | | | | I | | | | | | |
| 248 | | | | | | | V | | | | | | |
| 36 | | P | | | | | I | | | | | | |

With the exception of Gly668, one or more substitutions that putatively reduce the accuracy of DNA synthesis were observed for each of the 9 non-conserved amino acids. Eleven mutants harbored substitutions at either Ala661 or Thr664, including several single mutants. This initial screen with crude extracts suggested that a large number of changes are permitted in the O-helix that do not reduce the ability of Taq DNA polymerase I to complement the growth defect of recA718 polA12. Many of the substitutions in the O-helix that do not reduce the ability of Taq DNA polymerase I to carry out functional complementation reduce the fidelity of DNA synthesis in vitro.

To demonstrate that the reduction in fidelity exhibited by crude extracts is due to mutant Taq DNA polymerase I, wild type enzyme was purified as well as the three single mutants Ala661Glu, Ala661Pro and Thr664Arg. The mutant Ile665Thr, a mutant predicted to have no alteration in fidelity based on complementation assays, was also purified as a control. The mutated enzymes retained at least 29% of wild type activity in vitro, which is in accord with their ability to complement the growth defect caused in *E. coli* by temperature-sensitive host DNA polymerase I and ensures that analysis of fidelity will not be complicated by major impairments of catalytic efficiency.

Primer extension assays were carried out with the homogenous mutant polymerases. Wild type Taq DNA polymerase I extended most of the primer to one nucleotide before the template position opposite the missing complementary dNTP in a 5 min reaction. Only about 30% of the primers were elongated further. In reactions containing equivalent activity, the mutant polymerases Ala661Glu, Thr664Arg and Ala661Pro extended a larger proportion of the primers past the sites where the wild type polymerase ceased synthesis. The control enzyme Ile665Thr yielded an elongation pattern similar to that of the wild type enzyme. Elongation reactions with the three polymerases were also carried out for 60 min. Again, Ala661Glu and Thr664Arg synthesized a greater proportion of longer products than obtained with the wild type and Ile665Thr polymerases. Notably, Ala661Glu, Thr664Arg and Ala661Pro synthesized longer products in 5 min than the wild type did in 60 min.

To further analyze the reduced fidelity exhibited by the low fidelity polymerase mutants, a time course of primer elongation was carried out. Wild type Taq DNA polymerase I extended 9% of the primers past the first deoxyguanosine template residue within the 60 min incubation period, but elongation past the second deoxyguanosine was not detected. In the same interval, Thr664Arg extended 93% of the primer past the first template deoxyguanosine, and elongation proceeded past as many as five template deoxyguanosines. Importantly, a comparable proportion of primers was extended at all time points, despite the striking difference in the length of the products. These time course data indicate that greater elongation reflects increased ability to utilize non-complementary substrates and primer termini, rather than a putative difference in the amount of activity present.

In a forward mutation assay, the fidelity of DNA synthesis by the purified polymerases was quantitated by measuring the frequency of mutations produced by copying a biologically active template in vitro (Kunkel and Loeb, *J. Biol. Chem* 254:5718-5725 (1979)). The target sequence was the lacZ∀ gene located within a single-stranded region in gapped circular double-stranded M13mp2 DNA (Feig and Loeb, *Biochemistry* 32:4466-4473 (1993)). The gapped segment was filled by synthesis with the wild type or mutant enzymes. The double-stranded circular product was transfected into *E. coli*, and the mutation frequency was determined by scoring white and pale blue mutant plaques. A comparison of the specific activities and mutation frequencies of the purified enzymes is presented in Table II. After synthesis by wild type Taq DNA polymerase I, the mutation frequency was not greater than that of the uncopied control. Synthesis by Ala661Glu and Thr664Arg gave rise to mutation frequencies more than 7- and 25-fold greater, respectively, than that of the wild type polymerase.

TABLE II

Mutation Frequency in the lacZ ∀ Forward Mutation Assay

| Taq Pol I | Specific Activity units/mg | Plaques Scored Total | Mutant | Mutation Frequency $\times 10^{-3}$ |
| --- | --- | --- | --- | --- |
| WT | 66,000 | 8,637 | 22 | 2.5 |
| A661E | 45,000 | 6,782 | 116 | 17.1 |
| T664R | 23,000 | 5,148 | 324 | 62.9 |

A sample of independent, randomly chosen mutants produced by Thr664Arg was characterized by DNA sequence analysis using a THERMO SEQUENASE cycle sequencing kit (Amersham Life Science, Cleveland, Ohio). Both base substitutions and frameshifts were found throughout the targeted lacZ∀ gene and its regulatory sequence. Of the 64 independent plaques, 57 had mutations in the target. Other mutations presumably occurred outside the target region. Some had more than one base substitution and a total of 66 mutations were observed (see FIG. 3). Among them, 61 were base substitutions. Transitions (38/61.) were more frequent than transversions (23/61). T-C transitions accounted for 31 of 61 base substitutions, while T-A (9/61), A-T (8/61) and G-A (5/61) substitutions were less frequent. This base substitution spectrum is essentially the same as that reported for wild type Taq DNA polymerase I (Tindall and Kunkel, supra, 1988). From these data, the base substitution fidelity of Thr664Arg can be calculated as $8.6 \times 10^{-4}$ or 1 error per 1200 nucleotides. On the basis of the five frameshift mutants detected, the frameshift error can be calculated as $4.9 \times 10^5$ or 1 error per 20,000 nucleotides.

These results show that low fidelity Taq DNA polymerase I mutants were identified from a randomized library using a genetic complementation screen. The fidelity of Taq DNA polymerase I mutants was determined by primer extension assays and forward mutation assays.

EXAMPLE V

Identification of High Fidelity Taq DNA Polymerase I Mutants

This example shows the identification of high fidelity Taq DNA polymerase I mutants.

The active Taq DNA polymerase I mutants identified in Example II were assayed by the methods described in Example III to identify high fidelity mutants. A panel of 75 active polymerases was screened. Candidate high fidelity polymerase mutants are shown in Table III.

TABLE III

Candidate High Fidelity Mutants of Taq DNA Polymerase I

| WT | 659 R | R | A | A | 663 K | T | I | N | 667 F | G | V | L | 671 Y |
|---|---|---|---|---|---|---|---|---|---|---|---|---|---|
| FL |  |  |  |  |  |  |  |  | L |  |  |  |  |
| 74 |  | 3 |  |  |  | T |  |  | L |  |  |  |  |
| 146 |  |  |  |  |  |  |  | D |  |  |  |  |  |
| 147 |  |  |  |  |  |  |  | I |  |  |  |  |  |
| 149 |  |  |  |  |  |  | I | D |  |  |  |  |  |
| 169 |  | S |  |  |  |  |  |  |  |  |  | L |  |
| 186 |  |  |  |  | L |  |  |  |  |  |  |  |  |
| 219 |  |  |  |  |  | P | V | Y |  |  |  |  |  |
| 254 |  |  |  |  |  |  |  |  |  |  |  | V |  |
| 407 | Y |  |  |  |  |  |  |  |  |  |  |  |  |
| 424 |  |  |  |  |  |  |  |  | Y |  |  |  |  |
| 426 |  | S |  |  |  |  |  |  |  |  |  |  |  |
| 487 |  |  |  |  |  |  |  |  |  | R |  |  |  |
| 488 | K |  |  |  |  |  |  |  |  |  |  |  |  |
| 530 |  |  |  |  |  |  |  |  |  | S |  |  |  |
| 614 |  |  |  |  |  |  |  |  |  | Q |  |  |  |

Thirteen of the active polymerases exhibited greater accuracy in DNA synthesis. Table IV summarizes the results of a forward mutation assay of some of these high fidelity mutants. Several polymerase mutants displayed higher fidelity than the wild type Taq DNA polymerase. Polymerase mutants exhibiting particularly high fidelity are mutant 424, with Phe667Tyr, mutant 426, with Arg660Ser and mutant 488, with Arg660Lys.

TABLE IV

Fidelity of Taq DNA Polymerase Mutants in a lacZ Forward Mutation Assay

| Enzyme | Total Plaques | Mutant Plaques | Mutation Frequency $\times 10^{-3}$ |
|---|---|---|---|
| Wild Type | 5680 | 49 | 8.6 |
| High Fidelity Mutants | | | |
| MS147 | 7249 | 47 | 6.5 |
| MS169 | 7275 | 34 | 5.1 |
| MS254 | 6898 | 40 | 5.8 |
| MS424 | 4810 | 14 | 2.7 |
| MS426 | 5727 | 23 | 4.1 |
| MS488 | 3442 | 13 | 1.5 |
| Low Fidelity Mutant | | | |
| MS206 | 3333 | 13 | 40 |

These results show that Taq DNA polymerase mutants were identified and found to exhibit higher fidelity than wild type Taq DNA polymerase.

EXAMPLE VI

High Fidelity Tag DNA Polymerase Mutants Enhance the Sensitivity of Mismatch PCR-Based Assays for Somatic Mutations This example shows the use of high fidelity mutants obtained by mutating the active site O-helix of Taq DNA polymerase Ito enhance the sensitivity of mismatch PCR-based assays for somatic mutations.

Mismatch PCR is the basis of allele-specific identification of inherited mutations within genes and somatic mutations that occur in tumors. In these studies, one compares the extension of a correctly matched primer with the lack of extension using a primer with a 3'-terminal mismatch. The rate of extension by DNA polymerase using a primer with a single mismatch compared to a primer with a 3'-complementary base pair (matched) terminus is approximately $10^{-5}$ (Perinno and Loeb, J. Biol. Chem. 262:2898-2905 (1989)). Elongation from a double mismatch is even less frequent, and thus offers an even more stringent test of the inability of mutant Taq DNA polymerases to elongate a mismatched primer terminus.

A template containing the wild type sequence of human DNA polymerase-β at nucleotide positions 886-889 (CC CCTGGG) was utilized. PCR reactions were carried out with two complementary primers that flank the sequence (matched) or with one matched template and a second mismatched template containing a terminally mismatched primer with AA at the 3' terminal position. The AA would be across from the CC (underlined) in the template strand. In these studies, the ratio of templates containing the complementary and non-complementary sequences were varied. The PCR amplified product was separated by polyacrylamide gel electrophoresis and quantitated by phosphoimage analysis. Wild type Taq DNA polymerase detected one molecule of template containing a TT substitution in place of the two template CC when present in a population of $10^5$ molecules containing the non-mutant templates with the CC substitution. In contrast, both of the high fidelity Taq DNA polymerase mutants, with substitutions Phe667Tyr and Arg659Ser, detected one molecule of the TT template amongst $10^8$ molecules of the CC template when the primer contained two terminal 3'-AA nucleotide residues.

These results show that high fidelity Taq DNA polymerase mutants have two to three orders of magnitude enhanced sensitivity for detecting mutant DNA using a mismatch PCR-based assay.

EXAMPLE VII

High Fidelity Tap DNA Polymerase Mutants Enhance Sensitivity of Detection of Repetitive DNA Sequences This example demonstrates the use of high fidelity polymerase mutants to enhance the sensitivity and accuracy of amplifying repetitive DNA sequences.

Detection of the length of unstable microsatellite DNA in certain human tumors has depended on PCR amplification of specific sequences and determination of changes in electrophoretic mobility in gels. Due to the slippage of DNA polymerase while copying repetitive DNA, the interpretation of the results of this method have remained unsatisfactory.

High fidelity Taq DNA polymerases are identified using the methods described in Examples I and III. DNA templates containing runs of CA repeats with the number of repeats varying from 5 to 50 are used to test high fidelity Taq DNA polymerase mutants. After 20 to 70 rounds of PCR amplification, the product of the reaction is displayed on polyacrylamide gels. High fidelity polymerase mutants which display less slippage errors copying the repetitive sequences are identified. These high fidelity polymerase mutants are used to amplify repetitive DNA sequences in samples, for example tissue or tumor samples.

These results show that high fidelity mutants having enhanced sensitivity and accuracy in amplifying repetitive DNA sequences can be identified and used to amplify repetitive DNA in tissue or tumor samples.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. An isolated thermostable Taq DNA polymerase mutant having altered fidelity, wherein said mutant comprises one or more mutated amino acid residues in the active site O-helix of a thermostable polymerase, wherein said mutated amino acid residue is adjacent to an immutable or nearly immutable residue corresponding to Arg659, Lys663, Phe667 or Tyr671 of SEQ ID NO:2, wherein at least one mutation comprises a residue corresponding to Phe667Leu, and, optionally, additional mutations selected from the group of residues corresponding to:

Asn666Asp; Asn666Ile; Ile665Leu; Leu670Val; Arg660Tyr; Arg660Ser; Gly668Arg; Arg660Lys; Gly668Ser; Gly668Gln; Thr664Ile and Asn666Asp; Ala661Ser and Val669Leu; Ala661Glu, and Ile665Thr; and Thr664Pro, Ile665Val and Asn666Tyr of SEQ ID NO:2; and said Arg659 and Lys663 residues are not mutated.

2. The polymerase mutant of claim 1, wherein said polymerase mutant is a high fidelity mutant.

3. A method for identifying one or more mutations in a gene, comprising amplifying said gene using the high fidelity polymerase mutant of claim 2 under conditions which allow polymerase chain reaction amplification.

4. A method for accurately copying repetitive nucleotide sequences, comprising amplifying said repetitive nucleotide sequence using said high fidelity polymerase mutant of claim 2.

5. A method for diagnosing a genetic disease, comprising amplifying a gene using said high fidelity polymerase mutant of claim 2.

6. A method for identifying one or more mutations in a gene, comprising amplifying said gene using a high fidelity polymerase mutant of claim 1 under conditions which allow polymerase chain reaction amplification.

7. The method of claim 6, wherein said gene is amplified by exposing the strands of said gene to repeated cycles of denaturing, annealing and elongation to produce an amplified product.

8. The method of claim 7, further comprising determining the presence or absence of one or more mutations in the sequence of said gene.

9. A method for accurately copying repetitive nucleotide sequences, comprising amplifying said repetitive nucleotide sequence using a high fidelity polymerase mutant of claim 1.

10. The method of claim 9, wherein said repetitive nucleotide sequence is in a gene.

11. The method of claim 9, wherein said repetitive nucleotide sequence is in a microsatellite between genes.

12. A method for determining an inherited mutation, comprising amplifying a gene using a high fidelity polymerase mutant of claim 1.

13. A method for diagnosing a genetic disease, comprising correlating the inherited mutation determined in claim 12 with said genetic disease.

14. A method for diagnosing a genetic disease, comprising amplifying a gene using a high fidelity polymerase mutant of claim 1.

15. The method of claim 14, wherein said genetic disease comprises mutations in microsatellite or repetitive DNA.

16. The method of claim 15, wherein said genetic disease is cancer.

17. A method for determining the prognosis of a genetic disease, comprising amplifying a gene using a high fidelity polymerase mutant of claim 1.

18. An isolated thermostable polymerase comprising one or more mutated amino acid residues relative to a parent polymerase, wherein the mutant polymerase has increased ability to terminate polymerization when it encounters a template nucleotide complementary to a nucleoside triphosphate which is not present wherein at least one mutation comprises a residue corresponding to Phe667Leu, and, optionally, additional mutations are selected from the group of residues corresponding to:

Asn666Asp; Asn666Ile; Ile665Leu; Leu670Val; Arg660Tyr; Arg660Ser; Gly668Arg; Arg660Lys; Gly668Ser; Gly668Gln; Thr664Ile and Asn666Asp; Ala661Ser and Val669Leu; Ala661Glu and Ile665Thr; and Thr664Pro, Ile665Val and Asn666Tyr of SEQ ID NO:2.

19. The polymerase of claim 18, wherein the parent polymerase is selected from the group consisting of:

A DNA polymerase; a DNA-dependent RNA polymerase; a reverse transcriptase;
and a Taq polymerase.

20. The polymerase of claim 18, wherein said parent polymerase is Taq polymerase of SEQ ID NO: 2 or a polymerase with structurally similar domains as defined by a crystallographic molecular model.

21. The polymerase of claim 18, wherein said mutant polymerase is generated using random mutagenesis of said parent polymerase.

22. A reaction mixture comprising the polymerase of claim 18.

23. The reaction mixture of claim 22, further comprising at least one oligonucleotide primer.

24. The reaction mixture of claim 23, wherein said oligonucleotide primer is specific for a target associated with a genetic disease.

25. The reaction mixture of claim 24, wherein the target is a repetitive DNA sequence.

26. The reaction mixture of claim 24, wherein the target is a microsatellite.

27. The reaction mixture of claim 24, wherein the target involves a mutation selected from the group consisting of:
a point mutation, an insertion, and a deletion.

28. The reaction mixture of claim 22, wherein said reaction is for a polymerase chain reaction (PCR).

* * * * *

SEQUENCE LISTING

<160> NUMBER OF SEQ ID NOS: 61

<210> SEQ ID NO 1
<211> LENGTH: 2626
<212> TYPE: DNA
<213> ORGANISM: Thermus aquaticus

<400> SEQUENCE: 1

```
aagctcagat ctacctgcct gagggcgtcc ggttccagct ggcccttccc gaggggggaga      60 gggaggcgtt tctaaaagcc cttcaggacg ctacccgggg gcgggtggtg aagggtaac      120 atgaggggga tgctgcccct ctttgagccc aagggccggg tcctcctggt ggacggccac      180
cacctggcct accgcacctt ccacgccctg aagggcctca ccaccagccg ggggggagccg      240 gtgcaggcgg tctacggctt cgccaagagc ctcctcaagg ccctcaagga ggacggggac      300
gcggtgatcg tggtctttga cgccaaggcc ccctccttcc gccacgaggc ctacggggggg      360 tacaaggcgg gccgggcccc cacgccggag gactttcccc ggcaactcgc cctcatcaag      420
gagctggtgg acctcctggg gctggcgcgc ctcgaggtcc cgggctacga ggcggacgac      480
gtcctggcca gcctggccaa gaaggcggaa aaggagggct acgaggtccg catcctcacc      540
gccgacaaag acctttacca gctcctttcc gaccgcatcc acgtcctcca ccccgagggg      600
tacctcatca ccccggcctg gctttgggaa aagtacggcc tgaggcccga ccagtgggcc      660
gactaccggg ccctgaccgg ggacgagtcc gacaaccttc ccggggtcaa gggcatcggg      720
gagaagacgg cgaggaagct tctggaggag tgggggagcc tggaagccct cctcaagaac      780
ctggaccggc tgaagcccgc catccgggag aagatcctgg cccacatgga cgatctgaag      840
ctctcctggg acctggccaa ggtgcgcacc gacctgcccc tggaggtgga cttcgccaaa      900
aggcgggagc ccgaccggga gaggcttagg gcctttctgg agaggcttga gtttggcagc      960
ctcctccacg agttcggcct tctggaaagc cccaaggccc tggaggaggc ccctggccc      1020 ccgccggaag gggccttcgt gggctttgtg ctttcccgca aggagcccat gtgggccgat     1080
cttctggccc tggccgccgc cagggggggc cgggtccacc gggcccccga gccttataaa     1140
gccctcaggg acctgaagga ggcgcggggg cttctcgcca aagacctgag cgttctggcc     1200
ctgagggaag gccttggcct cccgcccggc gacgacccca tgctcctcgc ctacctcctg     1260
gacccttcca acaccacccc cgagggggtg gcccggcgct acggcgggga gtggacggag     1320
gaggcggggg agcgggccgc cctttccgag aggctcttcg ccaacctgtg ggggaggctt     1380 gaggggggagg agaggctcct ttggctttac cgggaggtgg agaggcccct ttccgctgtc     1440
ctggcccaca tggaggccac gggggtgcgc ctggacgtgg cctatctcag ggccttgtcc     1500
ctggaggtgg ccgaggagat cgcccgcctc gaggccgagg tcttccgcct ggccggccac      1560
```

```
ccctctcaacc tcaactcccg ggaccagctg gaaagggtcc tctttgacga gctagggctt    1620
cccgccatcg gcaagacgga gaagaccggc aagcgctcca ccagcgccgc cgtcctggag    1680
gccctccgcg aggcccaccc catcgtggag aagatcctgc agtaccggga gctcaccaag    1740
ctgaagagca cctacattga ccccttgccg gacctcatcc accccaggac gggccgcctc    1800
cacacccgct tcaaccagac ggccacggcc acgggcaggc taagtagctc cgatcccaac    1860
ctccagaaca tccccgtccg caccccgctt gggcagagga tccgccgggc cttcatcgcc    1920
gaggaggggt ggctattggt ggccctggac tatagccaga tagagctcag ggtgctggcc    1980
cacctctccg cgacgagaa cctgatccgg gtcttccagg aggggcggga catccacacg    2040
gagaccgcca gctggatgtt cggcgtcccc cgggaggccg tggacccct gatgcgccgg    2100 gcggccaaga ccatcaactt cggggtcctc tacggcatgt cggcccaccg cctctcccag    2160
gagctagcca tcccttacga ggaggcccag gccttcattg agcgctactt tcagagcttc    2220
cccaaggtgc gggcctggat tgagaagacc ctggaggagg caggaggcg ggggtacgtg    2280 gagaccctct tcggccgccg ccgctacgtg ccagacctag aggcccgggt gaagagcgtg    2340
cgggaggcgg ccgagcgcat ggccttcaac atgcccgtcc agggcaccgc cgccgacctc    2400
atgaagctgg ctatggtgaa gctcttcccc aggctggagg aaatgggggc aggatgctc    2460 cttcaggtcc acgacgagct ggtcctcgag gcccaaaag agaggcgga ggccgtggcc    2520 cggctggcca aggaggtcat ggaggggtg tatccctgg ccgtgccct ggaggtggag    2580 gtggggatag ggaggactg gctctccgcc aaggagtgat accacc                   2626
```

<210> SEQ ID NO 2
<211> LENGTH: 832
<212> TYPE: PRT
<213> ORGANISM: Thermus aquaticus

<400> SEQUENCE: 2

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190
```

```
Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
            245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro Pro Glu Gly
            290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
```

-continued

```
                610                 615                 620
Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 3
<211> LENGTH: 39
<212> TYPE: DNA
<213> ORGANISM: Artificial
<220> FEATURE:
<223> OTHER INFORMATION: Synthetic oligonucleotide sequence SacII-2

<400> SEQUENCE: 3
gggtccacgg cctcccgcgg gacgccgaac atccagctg                              39

<210> SEQ ID NO 4
<211> LENGTH: 16
<212> TYPE: DNA
<213> ORGANISM: Artificial
<220> FEATURE:
<223> OTHER INFORMATION: Synthetic oligonucleotide sequence DUM-U

<400> SEQUENCE: 4
ggactgcata tgactg                                                       16

<210> SEQ ID NO 5
<211> LENGTH: 22
<212> TYPE: DNA
<213> ORGANISM: Artificial
<220> FEATURE:
<223> OTHER INFORMATION: Synthetic oligonucleotide sequence DUM-D

<400> SEQUENCE: 5
ctagcagtca tatgcagtcc gc                                                22

<210> SEQ ID NO 6
<211> LENGTH: 80
```

-continued

```
<212> TYPE: DNA
<213> ORGANISM: Artificial
<220> FEATURE:
<223> OTHER INFORMATION: Synthetic oligonucleotide sequence O + 9 Random

<400> SEQUENCE: 6
cgggaggccg tggacccct gatgcgccgg gcggccaaga ccatcaactt cggggtcctc        60
tacggcatgt cggcccaccg                                                   80

<210> SEQ ID NO 7
<211> LENGTH: 37
<212> TYPE: DNA
<213> ORGANISM: Artificial
<220> FEATURE:
<223> OTHER INFORMATION: Synthetic oligonucleotide sequence O - 0 Random

<400> SEQUENCE: 7
tggctagctc ctgggagagg cggtgggccg acatgcc                                37

<210> SEQ ID NO 8
<211> LENGTH: 32
<212> TYPE: DNA
<213> ORGANISM: Artificial
<220> FEATURE:
<223> OTHER INFORMATION: Oligonucleotide O(+) Primer

<400> SEQUENCE: 8
ttcggcgtcc cgcgggaggc cgtggacccc ct                                     32

<210> SEQ ID NO 9
<211> LENGTH: 24
<212> TYPE: DNA
<213> ORGANISM: Artificial
<220> FEATURE:
<223> OTHER INFORMATION: Oligonucleotide O(-) Primer

<400> SEQUENCE: 9
gtaagggatg gctagctcct ggga                                              24

<210> SEQ ID NO 10
<211> LENGTH: 14
<212> TYPE: DNA
<213> ORGANISM: Artificial
<220> FEATURE:
<223> OTHER INFORMATION: Oligonucleotide Primer used in primer extension
      assay

<400> SEQUENCE: 10
cgcgccgaat tccc                                                         14

<210> SEQ ID NO 11
<211> LENGTH: 46
<212> TYPE: DNA
<213> ORGANISM: Artificial
<220> FEATURE:
<223> OTHER INFORMATION: Oligonucleotide template used in primer
      extension assay

<400> SEQUENCE: 11
gcgcggaagc ttggctgcag aatattgcta gcgggaattc ggcgcg                      46

<210> SEQ ID NO 12
<211> LENGTH: 13
<212> TYPE: PRT
<213> ORGANISM: Thermus aquaticus

<400> SEQUENCE: 12
```

```
Arg Arg Ala Ala Lys Thr Ile Asn Phe Gly Val Leu Tyr
1               5                   10

<210> SEQ ID NO 13
<211> LENGTH: 13
<212> TYPE: PRT
<213> ORGANISM: Artificial
<220> FEATURE:
<223> OTHER INFORMATION: Mutant region of Taq DNA polymerase I
<220> FEATURE:
<221> NAME/KEY: VARIANT
<222> LOCATION: (3)..(3)
<223> OTHER INFORMATION: Xaa at position 3 is Ser, Glu, Pro, Gly, Lys,
      or Arg

<400> SEQUENCE: 13

Arg Arg Xaa Ala Lys Thr Ile Asn Phe Gly Val Leu Tyr
1               5                   10

<210> SEQ ID NO 14
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 14

Arg Arg Ala Ser Lys Thr Ile Asn Phe Gly Val Leu Tyr
1               5                   10

<210> SEQ ID NO 15
<211> LENGTH: 13
<212> TYPE: PRT
<213> ORGANISM: Artificial
<220> FEATURE:
<223> OTHER INFORMATION: Mutant region of Taq DNA polymerase I
<220> FEATURE:
<221> NAME/KEY: VARIANT
<222> LOCATION: (6)..(6)
<223> OTHER INFORMATION: Xaa at position 6 is Ser, Asn, Ile, Pro, Arg,
      or His

<400> SEQUENCE: 15

Arg Arg Ala Ala Lys Xaa Ile Asn Phe Gly Val Leu Tyr
1               5                   10

<210> SEQ ID NO 16
<211> LENGTH: 13
<212> TYPE: PRT
<213> ORGANISM: Artificial
<220> FEATURE:
<223> OTHER INFORMATION: Mutant region of Taq DNA polymerase I
<220> FEATURE:
<221> NAME/KEY: VARIANT
<222> LOCATION: (7)..(7)
<223> OTHER INFORMATION: Xaa at position 7 is Val, Thr, or Leu

<400> SEQUENCE: 16

Arg Arg Ala Ala Lys Thr Xaa Asn Phe Gly Val Leu Tyr
1               5                   10

<210> SEQ ID NO 17
<211> LENGTH: 13
<212> TYPE: PRT
<213> ORGANISM: Artificial
<220> FEATURE:
<223> OTHER INFORMATION: Mutant region of Taq DNA polymerase I
<220> FEATURE:
<221> NAME/KEY: VARIANT
<222> LOCATION: (8)..(8)
```

<223> OTHER INFORMATION: Xaa at position 8 is Ile, Asp, or Val

<400> SEQUENCE: 17

Arg Arg Ala Ala Lys Thr Ile Xaa Phe Gly Val Leu Tyr
1               5                   10

<210> SEQ ID NO 18
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 18

Arg Arg Ala Ala Lys Thr Ile Asn Phe Gly Ile Leu Tyr
1               5                   10

<210> SEQ ID NO 19
<211> LENGTH: 13
<212> TYPE: PRT
<213> ORGANISM: Artificial
<220> FEATURE:
<223> OTHER INFORMATION: Mutant region of Taq DNA polymerase I
<220> FEATURE:
<221> NAME/KEY: VARIANT
<222> LOCATION: (12)..(12)
<223> OTHER INFORMATION: Xaa at position 12 is Ile, Thr, or Val

<400> SEQUENCE: 19

Arg Arg Ala Ala Lys Thr Ile Asn Phe Gly Val Xaa Tyr
1               5                   10

<210> SEQ ID NO 20
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 20

Arg Arg Ala Ala Lys Thr Ile Asn Phe Gly Val Leu Phe
1               5                   10

<210> SEQ ID NO 21
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 21

Arg Arg Ala Ala Lys Pro Ile Asn Phe Gly Val Phe Tyr
1               5                   10

<210> SEQ ID NO 22
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 22

Arg Arg Ala Ala Lys Pro Ile Asn Phe Gly Ile Leu Tyr
1               5                   10

<210> SEQ ID NO 23
<211> LENGTH: 13
<212> TYPE: PRT

```
<213> ORGANISM: Artificial
<220> FEATURE:
<223> OTHER INFORMATION: Mutant region of Taq DNA polymerase I

<400> SEQUENCE: 23

Arg Arg Ser Ala Lys Thr Val Asn Phe Gly Val Leu Tyr
1               5                   10

<210> SEQ ID NO 24
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 24

Arg Arg Ala Ser Lys Ser Ile Asn Phe Gly Val Leu Tyr
1               5                   10

<210> SEQ ID NO 25
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 25

Arg Arg Glu Ala Lys Ala Ile Asn Phe Gly Val Leu Tyr
1               5                   10

<210> SEQ ID NO 26
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 26

Arg Arg Arg Ala Lys Ser Ile Asn Phe Gly Val Leu Tyr
1               5                   10

<210> SEQ ID NO 27
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 27

Arg Arg Thr Ala Lys Arg Ile Asn Phe Gly Val Leu Tyr
1               5                   10

<210> SEQ ID NO 28
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 28

Arg Arg Pro Ala Lys Leu Ile Asn Phe Gly Val Leu Tyr
1               5                   10

<210> SEQ ID NO 29
<211> LENGTH: 13
<212> TYPE: PRT
<213> ORGANISM: Artificial
<220> FEATURE:
```

-continued

<223> OTHER INFORMATION: Mutant region of Taq DNA polymerase I

<400> SEQUENCE: 29

Arg Arg Ala Ala Lys Ser Ile Asn Phe Gly Ile Leu Tyr
1               5                   10

<210> SEQ ID NO 30
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 30

Arg Arg Ala Ser Lys Thr Ile Asn Phe Gly Ile Leu Tyr
1               5                   10

<210> SEQ ID NO 31
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 31

Arg Arg Ala Ser Lys Thr Ile Asn Phe Gly Thr Leu Tyr
1               5                   10

<210> SEQ ID NO 32
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 32

Arg Arg Arg Ala Lys Thr Ile Asn Phe Gly Val Leu Phe
1               5                   10

<210> SEQ ID NO 33
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 33

Pro Arg Ala Ala Lys Thr Ile Asn Phe Gly Val Thr Tyr
1               5                   10

<210> SEQ ID NO 34
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 34

Arg Arg Ala Ala Lys Ile Ile Asp Phe Gly Val Leu Tyr
1               5                   10

<210> SEQ ID NO 35
<211> LENGTH: 13
<212> TYPE: PRT
<213> ORGANISM: Artificial
<220> FEATURE:
<223> OTHER INFORMATION: Mutant region of Taq DNA polymerase I

```
<400> SEQUENCE: 35

Arg Arg Ala Ala Lys Arg Ile Ile Phe Gly Val Leu Tyr
1               5                   10

<210> SEQ ID NO 36
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 36

Arg Arg Ala Ala Lys Ser Ile Asn Phe Gly Val Leu Phe
1               5                   10

<210> SEQ ID NO 37
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 37

Arg Arg Ser Ala Lys Thr Ile Asn Phe Gly Leu Leu Tyr
1               5                   10

<210> SEQ ID NO 38
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 38

Trp Arg Ala Ala Lys Lys Ile Asn Phe Gly Val Leu Tyr
1               5                   10

<210> SEQ ID NO 39
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 39

Arg Arg Ala Ala Lys Thr Ile Ile Phe Gly Val Thr Tyr
1               5                   10

<210> SEQ ID NO 40
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 40

Trp Arg Ala Ala Lys Pro Ile Asn Phe Gly Val Leu Tyr
1               5                   10

<210> SEQ ID NO 41
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 41
```

Arg Arg Ala Ala Lys Ser Thr Asn Phe Gly Val Leu Tyr
1               5                   10

<210> SEQ ID NO 42
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 42

Arg Arg Ala Gly Lys Asn Ile Asn Phe Gly Val Leu Tyr
1               5                   10

<210> SEQ ID NO 43
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 43

Arg Arg Gly Ala Lys Thr Ile Ile Phe Gly Val Leu Tyr
1               5                   10

<210> SEQ ID NO 44
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 44

Arg Arg Ala Ala Lys Ser Ser Asn Phe Gly Val Leu Tyr
1               5                   10

<210> SEQ ID NO 45
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 45

Arg Arg Glu Ala Lys Thr Thr Asn Phe Gly Val Leu Tyr
1               5                   10

<210> SEQ ID NO 46
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 46

Arg Arg Pro Ala Lys Ile Ile Asn Phe Gly Val Leu Tyr
1               5                   10

<210> SEQ ID NO 47
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 47

Arg Arg Pro Ala Lys Thr Ile Ile Phe Gly Val Leu Tyr
1               5                   10

```
<210> SEQ ID NO 48
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 48

Arg Arg Ala Ala Lys Asn Ile Asn Phe Gly Val Ile Tyr
1               5                   10

<210> SEQ ID NO 49
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 49

Arg Arg Ala Ala Lys Thr Thr Asn Phe Gly Val Leu Phe
1               5                   10

<210> SEQ ID NO 50
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 50

Arg Arg Pro Ala Lys Arg Ile Asn Phe Gly Leu Leu Tyr
1               5                   10

<210> SEQ ID NO 51
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 51

Arg Arg Thr Ala Lys Pro Val Asn Phe Gly Val Leu Tyr
1               5                   10

<210> SEQ ID NO 52
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 52

Arg Arg Glu Ala Lys Thr Thr Asn Leu Gly Val Leu Tyr
1               5                   10

<210> SEQ ID NO 53
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 53

Arg Arg Gly Ala Lys Thr Thr Asn Phe Gly Ile Leu Tyr
1               5                   10
```

```
<210> SEQ ID NO 54
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 54

Arg Arg Ala Ala Lys Pro Val Tyr Phe Gly Val Leu Tyr
1               5                   10

<210> SEQ ID NO 55
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 55

Gln Arg Pro Ala Lys Ser Ile Asn Phe Gly Val Leu Tyr
1               5                   10

<210> SEQ ID NO 56
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 56

Arg Arg Ala Ala Lys Arg Ile Ile Ile Gly Val Val Tyr
1               5                   10

<210> SEQ ID NO 57
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 57

Arg Arg Ser Gly Lys Ser Ile Ile Phe Gly Val Leu Tyr
1               5                   10

<210> SEQ ID NO 58
<211> LENGTH: 13
<212> TYPE: PRT
<213> ORGANISM: Artificial
<220> FEATURE:
<223> OTHER INFORMATION: Mutant region of Taq DNA polymerase I
<220> FEATURE:
<221> NAME/KEY: VARIANT
<222> LOCATION: (2)..(2)
<223> OTHER INFORMATION: Xaa at position 2 is Tyr, Pro, Gly, Ser, Ile,
      Lys, Trp, Cys, or Ala

<400> SEQUENCE: 58

Arg Xaa Ala Ala Lys Thr Ile Asn Phe Gly Val Leu Tyr
1               5                   10

<210> SEQ ID NO 59
<211> LENGTH: 13
<212> TYPE: PRT
<213> ORGANISM: Artificial
<220> FEATURE:
<223> OTHER INFORMATION: Mutant region of Taq DNA polymerase I

<400> SEQUENCE: 59

Arg Arg Ala Ala Lys Thr Ile Asn Tyr Gly Val Leu Tyr
```

-continued

```
1               5                   10

<210> SEQ ID NO 60
<211> LENGTH: 13
<212> TYPE: PRT
<213> ORGANISM: Artificial
<220> FEATURE:
<223> OTHER INFORMATION: Mutant region of Taq DNA polymerase I
<220> FEATURE:
<221> NAME/KEY: VARIANT
<222> LOCATION: (10)..(10)
<223> OTHER INFORMATION: Xaa at position 10 is Ser, Gln, Arg, or Lys

<400> SEQUENCE: 60

Arg Arg Ala Ala Lys Thr Ile Asn Phe Xaa Val Leu Tyr
1               5                   10

<210> SEQ ID NO 61
<211> LENGTH: 262
<212> TYPE: DNA
<213> ORGANISM: Artificial
<220> FEATURE:
<223> OTHER INFORMATION: Spectrum of single base changes generated in a
      forward mutation assay by Taq DNA polymerase I mutant Thr664Arg

<400> SEQUENCE: 61
gcgcaacgca aytaayrtra gttagchcac wcattaggca ccccaggcwh ymcrctttat      60
gcttccggct cgtaygtygt gyggaattgt gagcggayaa caatytcaca caggaaacag     120
ctahgwccat gattacgrww tcactggccg tcshytyhca acgtcdtgwc ygrgaaaacc     180
ctggcgytac ccaacttwat crccyygcag macatccccc ttycgccasc tggcgtaata    240
gcgaagaggc ccgcaccgat cg                                             262
```